United States Patent
Phillips

(10) Patent No.: US 11,135,351 B2
(45) Date of Patent: Oct. 5, 2021

(54) SYSTEMS AND METHODS FOR APPLYING REDUCED PRESSURE THERAPY

(71) Applicant: Smith & Nephew PLC, Watford (GB)

(72) Inventor: Marcus Damian Phillips, Wakefield (GB)

(73) Assignee: Smith & Nephew PLC, Watford (GB)

( * ) Notice: Subject to any disclaimer, the term of this patent is extended or adjusted under 35 U.S.C. 154(b) by 303 days.

(21) Appl. No.: 16/328,633

(22) PCT Filed: Aug. 29, 2017

(86) PCT No.: PCT/EP2017/071609
§ 371 (c)(1),
(2) Date: Feb. 26, 2019

(87) PCT Pub. No.: WO2018/041805
PCT Pub. Date: Mar. 8, 2018

(65) Prior Publication Data
US 2021/0038780 A1    Feb. 11, 2021

Related U.S. Application Data

(60) Provisional application No. 62/524,111, filed on Jun. 23, 2017, provisional application No. 62/381,210, filed on Aug. 30, 2016.

(51) Int. Cl.
*A61M 1/00* (2006.01)
*A61F 13/00* (2006.01)

(52) U.S. Cl.
CPC ......... *A61M 1/90* (2021.05); *A61F 13/00029* (2013.01); *A61F 13/00068* (2013.01)

(58) Field of Classification Search
CPC .. A61M 1/0088; A61M 1/0058; A61M 27/00; A61M 1/0023; A61M 1/0031;
(Continued)

(56) References Cited

U.S. PATENT DOCUMENTS 3,194,239 A    7/1965 Sullivan
3,789,851 A    2/1974 Leveen
(Continued)

FOREIGN PATENT DOCUMENTS

AU    2012261793 B2    11/2014
AU    2013206230 B2    5/2016
(Continued)

OTHER PUBLICATIONS

International Search Report and Written Opinion for Application No. PCT/EP2017/071609, dated Oct. 10, 2017, 15 pages.
(Continued)

*Primary Examiner* — Nicholas J Weiss
*Assistant Examiner* — Eric Rassavong
(74) *Attorney, Agent, or Firm* — Knobbe, Martens, Olson & Bear, LLP

(57) ABSTRACT

Embodiments disclosed herein are directed to the treatment of wounds using negative pressure. Some embodiments disclosed herein provide for a hydrophilic drainage layer, which may be suitable for use in abdominal wound sites, and which may be sized in a dimensionally-independent manner. Additional embodiments provide for an organ protection layer, as well as a system for the treatment of abdominal wounds.

19 Claims, 43 Drawing Sheets

US 11,135,351 B2
Page 2

(58) Field of Classification Search
CPC .......... A61M 1/00029; A61F 13/00068; A61F 13/0203; A61F 13/0216; A61F 2013/00536
See application file for complete search history.

(56) References Cited

U.S. PATENT DOCUMENTS

| | | | |
|---|---|---|---|
| 4,467,805 A | | 8/1984 | Fukuda |
| 4,608,041 A | | 8/1986 | Nielsen |
| 4,699,134 A | | 10/1987 | Samuelsen |
| 4,815,468 A | | 3/1989 | Annand |
| 5,034,006 A | * | 7/1991 | Hosoda .................. A61M 1/85 604/317 |
| 5,176,663 A | | 1/1993 | Svedman et al. |
| 5,264,218 A | | 11/1993 | Rogozinski |
| 5,376,067 A | | 12/1994 | Daneshvar |
| 5,409,472 A | | 4/1995 | Rawlings et al. |
| 5,415,715 A | | 5/1995 | Delage et al. |
| 5,423,857 A | | 6/1995 | Rosenman et al. |
| 5,437,651 A | * | 8/1995 | Todd .................. A61M 1/90 604/313 |
| 5,512,041 A | | 4/1996 | Bogart |
| 5,562,107 A | | 10/1996 | Lavender et al. |
| 5,584,859 A | | 12/1996 | Brotz |
| 5,636,643 A | | 6/1997 | Argenta et al. |
| 5,695,777 A | | 12/1997 | Donovan et al. |
| 6,176,868 B1 | | 1/2001 | Detour |
| 6,333,093 B1 | * | 12/2001 | Burrell .................. A61L 29/16 428/194 |
| 6,503,208 B1 | | 1/2003 | Skovlund |
| 6,548,727 B1 | | 4/2003 | Swenson |
| 6,566,575 B1 | | 5/2003 | Stickels et al. |
| 6,685,681 B2 | | 2/2004 | Lockwood et al. |
| 6,770,794 B2 | | 8/2004 | Fleischmann |
| 6,787,682 B2 | | 9/2004 | Gilman |
| 6,977,323 B1 | | 12/2005 | Swenson |
| 7,004,915 B2 | | 2/2006 | Boynton et al. |
| 7,144,390 B1 | | 12/2006 | Hannigan et al. |
| 7,315,183 B2 | | 1/2008 | Hinterscher |
| 7,351,250 B2 | | 4/2008 | Zamierowski |
| 7,361,184 B2 | | 4/2008 | Joshi |
| 7,438,705 B2 | | 10/2008 | Karpowicz et al. |
| 7,494,482 B2 | | 2/2009 | Orgill et al. |
| 7,615,036 B2 | | 11/2009 | Joshi et al. |
| 7,622,629 B2 | | 11/2009 | Aali |
| 7,625,362 B2 | | 12/2009 | Boehringer et al. |
| 7,683,667 B2 | | 3/2010 | Kim et al. |
| 7,700,819 B2 | | 4/2010 | Ambrosio et al. |
| 7,754,937 B2 | | 7/2010 | Boehringer et al. |
| 7,779,625 B2 | | 8/2010 | Joshi et al. |
| 7,815,616 B2 | | 10/2010 | Boehringer et al. |
| 7,857,806 B2 | | 12/2010 | Karpowicz et al. |
| 7,863,495 B2 | | 1/2011 | Aali |
| 7,892,181 B2 | | 2/2011 | Christensen et al. |
| 7,896,856 B2 | | 3/2011 | Petrosenko et al. |
| 7,909,805 B2 | | 3/2011 | Weston et al. |
| 7,910,789 B2 | | 3/2011 | Sinyagin |
| 7,931,774 B2 | | 4/2011 | Hall et al. |
| 7,942,866 B2 | | 5/2011 | Radl et al. |
| 7,951,124 B2 | | 5/2011 | Boehringer et al. |
| 7,964,766 B2 | | 6/2011 | Blott et al. |
| 7,976,519 B2 | | 7/2011 | Bubb et al. |
| 7,976,524 B2 | | 7/2011 | Kudo et al. |
| 8,030,534 B2 | | 10/2011 | Radl et al. |
| 8,057,447 B2 | | 11/2011 | Olson et al. |
| 8,062,331 B2 | | 11/2011 | Zamierowski |
| 8,067,662 B2 | | 11/2011 | Aali et al. |
| 8,070,773 B2 | | 12/2011 | Zamierowski |
| 8,114,126 B2 | | 2/2012 | Heaton et al. |
| 8,123,781 B2 | | 2/2012 | Zamierowski |
| 8,142,419 B2 | | 3/2012 | Heaton et al. |
| 8,172,816 B2 | | 5/2012 | Kazala, Jr. et al. |
| 8,187,237 B2 | | 5/2012 | Seegert |
| 8,188,331 B2 | | 5/2012 | Barta et al. |
| 8,197,467 B2 | | 6/2012 | Heaton et al. |
| 8,207,392 B2 | | 6/2012 | Haggstrom et al. |
| 8,235,955 B2 | | 8/2012 | Blott et al. |
| 8,246,590 B2 | | 8/2012 | Hu et al. |
| 8,257,328 B2 | | 9/2012 | Augustine et al. |
| 8,273,105 B2 | | 9/2012 | Cohen et al. |
| 8,328,776 B2 | | 12/2012 | Kelch et al. |
| 8,337,411 B2 | | 12/2012 | Nishtala et al. |
| 8,353,931 B2 | | 1/2013 | Stopek et al. |
| 8,357,131 B2 | | 1/2013 | Olson |
| 8,376,972 B2 | | 2/2013 | Fleischmann |
| 8,430,867 B2 | | 4/2013 | Robinson et al. |
| 8,447,375 B2 | | 5/2013 | Shuler |
| 8,454,990 B2 | | 6/2013 | Canada et al. |
| 8,460,257 B2 | | 6/2013 | Locke et al. |
| 8,469,935 B2 | * | 6/2013 | Simmons ................ A61M 1/90 604/313 |
| 8,481,804 B2 | | 7/2013 | Timothy |
| 8,486,032 B2 | | 7/2013 | Seegert et al. |
| 8,500,776 B2 | | 8/2013 | Ebner |
| 8,608,776 B2 | | 12/2013 | Coward et al. |
| 8,632,523 B2 | | 1/2014 | Eriksson et al. |
| 8,673,992 B2 | | 3/2014 | Eckstein et al. |
| 8,679,080 B2 | | 3/2014 | Kazala, Jr. et al. |
| 8,679,153 B2 | | 3/2014 | Dennis |
| 8,680,360 B2 | | 3/2014 | Greener et al. |
| 8,708,984 B2 | | 4/2014 | Robinson et al. |
| 8,721,629 B2 | | 5/2014 | Hardman et al. |
| 8,746,662 B2 | | 6/2014 | Poppe |
| 8,764,732 B2 | | 7/2014 | Hartwell |
| 8,791,315 B2 | | 7/2014 | Lattimore et al. |
| 8,791,316 B2 | | 7/2014 | Greener |
| 8,802,916 B2 | | 8/2014 | Edward et al. |
| 8,821,535 B2 | | 9/2014 | Greener |
| 8,945,030 B2 | | 2/2015 | Weston et al. |
| 9,044,579 B2 | | 6/2015 | Blott et al. |
| 9,061,095 B2 | | 6/2015 | Adie et al. |
| 9,180,231 B2 | | 11/2015 | Greener |
| 9,192,444 B2 | * | 11/2015 | Locke ............... A61F 13/00068 |
| 9,289,327 B2 | * | 3/2016 | Beard ............... A61F 13/00025 |
| 9,408,755 B2 | | 8/2016 | Larsson et al. |
| 9,421,132 B2 | | 8/2016 | Dunn et al. |
| 9,655,807 B2 | | 5/2017 | Locke et al. |
| 9,731,064 B2 | * | 8/2017 | Ruiz Soto ......... A61F 13/00068 |
| 9,849,023 B2 | | 12/2017 | Hall et al. |
| 2001/0034499 A1 | | 10/2001 | Sessions et al. |
| 2002/0077661 A1 | | 6/2002 | Saadat |
| 2002/0161346 A1 | | 10/2002 | Lockwood et al. |
| 2003/0040687 A1 | | 2/2003 | Boynton |
| 2004/0030304 A1 | * | 2/2004 | Hunt ................ A61L 15/22 604/317 |
| 2004/0162512 A1 | | 8/2004 | Liedtke et al. |
| 2004/0267312 A1 | | 12/2004 | Kanner et al. |
| 2005/0142331 A1 | | 6/2005 | Anderson et al. |
| 2005/0267424 A1 | | 12/2005 | Eriksson et al. |
| 2006/0020269 A1 | | 1/2006 | Cheng |
| 2006/0058842 A1 | | 3/2006 | Wilke et al. |
| 2006/0069357 A1 | | 3/2006 | Marasco |
| 2006/0217795 A1 | | 9/2006 | Besselink et al. |
| 2006/0271018 A1 | | 11/2006 | Korf |
| 2007/0052144 A1 | | 3/2007 | Knirck et al. |
| 2007/0104941 A1 | | 5/2007 | Kameda et al. |
| 2007/0118096 A1 | | 5/2007 | Smith et al. |
| 2007/0123973 A1 | | 5/2007 | Roth et al. |
| 2007/0129660 A1 | | 6/2007 | McLeod et al. |
| 2007/0149910 A1 | | 6/2007 | Zocher |
| 2007/0185426 A1 | | 8/2007 | Ambrosio et al. |
| 2007/0185463 A1 | | 8/2007 | Mulligan |
| 2007/0213597 A1 | | 9/2007 | Wooster |
| 2007/0282309 A1 | | 12/2007 | Bengtson et al. |
| 2008/0041401 A1 | | 2/2008 | Casola et al. |
| 2008/0108977 A1 | | 5/2008 | Heaton et al. |
| 2008/0243096 A1 | | 10/2008 | Svedman et al. |
| 2008/0275409 A1 | | 11/2008 | Kane et al. |
| 2009/0005716 A1 | | 1/2009 | Abuzaina et al. |
| 2009/0099519 A1 | | 4/2009 | Kaplan |
| 2009/0105670 A1 | | 4/2009 | Bentley et al. |
| 2009/0204423 A1 | | 8/2009 | Degheest et al. |
| 2010/0022990 A1 | | 1/2010 | Karpowicz et al. |
| 2010/0047324 A1 | | 2/2010 | Fritz et al. |

(56) References Cited

U.S. PATENT DOCUMENTS

| | | | |
|---|---|---|---|
| 2010/0081983 A1 | 4/2010 | Zocher et al. | |
| 2010/0137775 A1 | 6/2010 | Hu et al. | |
| 2010/0150991 A1 | 6/2010 | Bernstein | |
| 2010/0160874 A1 | 6/2010 | Robinson et al. | |
| 2010/0179515 A1 | 7/2010 | Swain et al. | |
| 2010/0198128 A1 | 8/2010 | Turnlund et al. | |
| 2010/0262106 A1 | 10/2010 | Hartwell | |
| 2010/0280468 A1 | 11/2010 | Haggstrom et al. | |
| 2010/0312159 A1 | 12/2010 | Aali et al. | |
| 2011/0021965 A1 | 1/2011 | Karp et al. | |
| 2011/0022082 A1 | 1/2011 | Burke et al. | |
| 2011/0059291 A1 | 3/2011 | Boyce et al. | |
| 2011/0066096 A1 | 3/2011 | Svedman | |
| 2011/0082480 A1 | 4/2011 | Viola | |
| 2011/0110996 A1 | 5/2011 | Schoenberger et al. | |
| 2011/0112458 A1 | 5/2011 | Holm et al. | |
| 2011/0178451 A1 | 7/2011 | Robinson et al. | |
| 2011/0224631 A1 | 9/2011 | Simmons et al. | |
| 2011/0224632 A1 | 9/2011 | Zimnitsky et al. | |
| 2011/0224634 A1 | 9/2011 | Locke et al. | |
| 2011/0264138 A1 | 10/2011 | Avelar et al. | |
| 2011/0270301 A1 | 11/2011 | Cornet et al. | |
| 2011/0305736 A1 | 12/2011 | Wieland et al. | |
| 2012/0016321 A1 | 1/2012 | Wu et al. | |
| 2012/0029455 A1 | 2/2012 | Perez-Foullerat et al. | |
| 2012/0059412 A1 | 3/2012 | Fleischmann | |
| 2012/0130327 A1 | 5/2012 | Marquez | |
| 2012/0136326 A1 | 5/2012 | Croizat et al. | |
| 2012/0136328 A1 | 5/2012 | Johannison et al. | |
| 2012/0143113 A1 | 6/2012 | Robinson et al. | |
| 2012/0172926 A1 | 7/2012 | Hotter | |
| 2012/0191132 A1 | 7/2012 | Sargeant | |
| 2012/0209226 A1 | 8/2012 | Simmons et al. | |
| 2012/0209227 A1 | 8/2012 | Dunn et al. | |
| 2012/0220960 A1* | 8/2012 | Ruland | A61M 1/90 604/291 |
| 2012/0253302 A1 | 10/2012 | Corley | |
| 2013/0150813 A1 | 6/2013 | Gordon et al. | |
| 2013/0197457 A1 | 8/2013 | Kazala, Jr. et al. | |
| 2013/0204213 A1 | 8/2013 | Heagle et al. | |
| 2013/0245527 A1 | 9/2013 | Croizat et al. | |
| 2013/0325142 A1 | 12/2013 | Hunter et al. | |
| 2013/0331757 A1 | 12/2013 | Belson | |
| 2014/0094730 A1 | 4/2014 | Greener et al. | |
| 2014/0163415 A1 | 6/2014 | Zaiken et al. | |
| 2014/0249495 A1 | 9/2014 | Mumby et al. | |
| 2015/0065968 A1 | 3/2015 | Sealy et al. | |
| 2015/0119837 A1 | 4/2015 | Thompson, Jr. et al. | |
| 2015/0157758 A1 | 6/2015 | Blücher et al. | |
| 2015/0190288 A1 | 7/2015 | Dunn et al. | |
| 2015/0196431 A1 | 7/2015 | Dunn et al. | |
| 2015/0216732 A1 | 8/2015 | Hartwell et al. | |
| 2015/0320434 A1 | 11/2015 | Ingram et al. | |
| 2015/0320602 A1 | 11/2015 | Locke et al. | |
| 2015/0374561 A1 | 12/2015 | Hubbard, Jr. et al. | |
| 2016/0144085 A1 | 5/2016 | Melin et al. | |
| 2016/0184496 A1 | 6/2016 | Jaecklein et al. | |
| 2017/0065751 A1 | 3/2017 | Toth et al. | |
| 2017/0281838 A1 | 10/2017 | Dunn | |

FOREIGN PATENT DOCUMENTS

| | | |
|---|---|---|
| CN | 101112326 A | 1/2008 |
| CN | 203408163 U | 1/2014 |
| DE | 2949920 A1 | 3/1981 |
| EP | 0 164319 A2 | 12/1985 |
| EP | 1320342 A1 | 6/2003 |
| EP | 2279016 A1 | 2/2011 |
| EP | 2567717 A1 | 3/2013 |
| EP | 2601984 A2 | 6/2013 |
| GB | 2389794 A | 12/2003 |
| GB | 2423019 A | 8/2006 |
| GB | 2489947 A | 10/2012 |
| GB | 2496310 A | 5/2013 |
| RU | 62504 U1 | 4/2007 |
| SU | 1818103 A1 | 5/1993 |
| WO | WO 01/85248 A1 | 11/2001 |
| WO | WO 01/89392 A2 | 11/2001 |
| WO | WO 02/05737 A1 | 1/2002 |
| WO | WO 03/003948 A1 | 1/2003 |
| WO | WO 2004/037334 A1 | 5/2004 |
| WO | WO 2005/046761 A1 | 5/2005 |
| WO | WO 2005/105174 A1 | 11/2005 |
| WO | WO 2006/046060 A2 | 5/2006 |
| WO | WO 2008/027449 A2 | 3/2008 |
| WO | WO 2008/064502 A1 | 6/2008 |
| WO | WO 2008/104609 A1 | 9/2008 |
| WO | WO 2009/112062 A1 | 9/2009 |
| WO | WO-2009111655 A2 | 9/2009 |
| WO | WO 2010/033725 A2 | 3/2010 |
| WO | WO 2010/097570 A1 | 9/2010 |
| WO | WO 2011/023384 A1 | 3/2011 |
| WO | WO 2012/082716 A2 | 6/2012 |
| WO | WO 2012/082876 A1 | 6/2012 |
| WO | WO 2012/136707 A1 | 10/2012 |
| WO | WO 2012/142473 A1 | 10/2012 |
| WO | WO 2013/012381 A1 | 1/2013 |
| WO | WO 2013/043258 A1 | 3/2013 |
| WO | WO 2013/071243 A2 | 5/2013 |
| WO | WO 2013/076450 A1 | 5/2013 |
| WO | WO 2013/079947 A1 | 6/2013 |
| WO | WO 2013/175309 A1 | 11/2013 |
| WO | WO 2013/175310 A2 | 11/2013 |
| WO | WO 2014/013348 A2 | 1/2014 |
| WO | WO 2014/140578 A1 | 9/2014 |
| WO | WO 2014/158526 A1 | 10/2014 |
| WO | WO 2014/165275 A1 | 10/2014 |
| WO | WO 2014/178945 A1 | 11/2014 |
| WO | WO 2014/194786 A1 | 12/2014 |
| WO | WO 2015/008054 A1 | 1/2015 |
| WO | WO 2015/061352 A2 | 4/2015 |
| WO | WO 2015/109359 A1 | 7/2015 |
| WO | WO 2015/110409 A1 | 7/2015 |
| WO | WO 2015/110410 A1 | 7/2015 |
| WO | WO 2015/169637 A1 | 11/2015 |
| WO | WO 2015/193257 A1 | 12/2015 |
| WO | WO 2016/018448 A1 | 2/2016 |
| WO | WO 2016/176513 A1 | 11/2016 |
| WO | WO 2016/179245 A1 | 11/2016 |
| WO | WO 2017/106576 A1 | 6/2017 |
| WO | WO 2018/038665 A1 | 3/2018 |
| WO | WO 2018/041805 A1 | 3/2018 |
| WO | WO 2018/044944 A1 | 3/2018 |
| WO | WO 2018/044949 A1 | 3/2018 |

OTHER PUBLICATIONS

"Definition or 3D Printer," American Heritage Dictionary of the English Language, Fifth Edition, accessed on Feb. 22, 2018 from URL: https://www.thefreedictionary.co, 2016, 1 page.

"Definition of Adhere," The Free Dictionary, accessed on Mar. 23, 2017 from http://www.thefreedictionary.com/adhere, 6 pages.

"Definition of Oculiform," Webster's Revised Unabridged Dictionary, accessed from The Free Dictionary on May 30, 2018 from URL: https://www.thefreedictionary.com/Oculiform, 1913, 1 page.

"Definition of Throughout," Merriam-Webster Dictionary, accessed on Aug. 29, 2017 from https://www.merriam-webster.com/dictionary/throughout, 11 pages.

Hougaard, et al., "The Open Abdomen: Temporary Closure with a Modified Negative Pressure Therapy Technique," International Wound Journal, ISSN 1742-4801, 2014, pp. 13-16.

Kapischke M., et al., "Self-Fixating Mesh for the Lichtenstein Procedure-a Prestudy," Langenbecks Arch Surg, 2010, vol. 395, pp. 317-322.

International Preliminary Report on Patentability for Application No. PCT/EP2017/071609, dated Mar. 14, 2019, 12 pages.

* cited by examiner

SYSTEMS AND METHODS FOR APPLYING REDUCED PRESSURE THERAPY

CROSS-REFERENCE TO RELATED APPLICATIONS

This application is a U.S. national stage application of International Patent Application No. PCT/EP2017/071609, filed Aug. 29, 2017, which claims priority to U.S. Provisional Application No. 62/524,111, filed Jun. 23, 2017 and U.S. Provisional Application No. 62/381,210, filed Aug. 30, 2016.

BACKGROUND

Field of Use

Embodiments of the present invention relate generally to the treatment of wounds using negative pressure wound therapy, and more specifically to an improved apparatus and method thereof to manage open abdominal wounds.

Description of the Related Art

The treatment of open or chronic wounds by means of applying negative pressure to the site of the wound, where the wounds are too large to spontaneously close or otherwise fail to heal is well known in the art. Negative pressure wound treatment systems currently known in the art commonly involve placing a cover that is impermeable to liquids over the wound, using various mechanisms to seal the cover to the tissue of the patient surrounding the wound, and connecting a source of negative pressure (such as a vacuum pump) to the cover whereby an area of negative pressure is created under the cover in the area of the wound.

When applying the negative pressure wound treatment system which is an essentially a sealed system to the abdomen, the ability of underlying layers of the system to draw wound fluid from wound site to the opening is important. Otherwise, accumulation of wound fluid may cause undesirable complications, such as formation of unwanted granulation tissue. Typically, in negative pressure wound therapy applied to the open abdomen, hydrophobic materials are used as the underlying layers. Hydrophobic materials are capable of providing a fluid flow path for large amounts of liquid from the abdomen with good distribution of negative pressure, but their ability to permit flow of aqueous liquid may be limited by their inherent absence of affinity with fluid.

SUMMARY

Embodiments of the invention disclosed herein are directed to a reduced pressure appliance and methods of treatment using a reduced pressure appliance, and may be useful in the treatment of wounds using reduced pressure.

Some embodiments of the appliance described herein may comprise a drainage layer or an underlying layer. The drainage layer or the underlying layer as described herein allows transmission of fluid such as air and liquids away from a wound site into upper layer(s) of the wound dressing. The drainage layer or the underlying layer also ensures that an open air channel can be maintained to communicate negative pressure over the wound area even when the dressing is handling substantial amounts of exudates. The layer should remain open under the typical pressures that will be applied during negative pressure wound therapy. Preferably, the layer remains open over an area corresponding to the wound site, and thereby ensures that the whole wound site sees an equalized negative pressure.

A drainage layer or an underlying layer may comprise voids or may comprise one or more materials which transmit fluid, or may be a combination thereof. The layer may incorporate other functional materials provided that it is still capable of transmitting negative pressure, and preferably also liquid fluids. In some embodiments, the underlying or drainage layer is capable of transmitting wound exudates and other compositions of matter. To resolve the limited fluid-drawing ability of hydrophobic underlying layers, some embodiments provide a negative pressure wound treatment system that uses hydrophilic material as one or more layers underlying a wound cover or drape.

In certain embodiments, a system for the treatment of a wound site using negative pressure comprises: a porous pad suitable for the transmission of negative pressure to a wound site; a drainage layer positioned under the porous pad, the drainage layer configured to channel fluid from the wound site; a flexible drape configured to be placed over the porous pad; a source of negative pressure; and a conduit configured to transmit negative pressure from the source to the flexible drape.

In some embodiments, the drainage layer may comprise a hydrophilic material such as a hydrophilic foam. The hydrophilic foam may comprise polyvinyl alcohol (PVA). In certain embodiments, the drainage layer may further comprise a top film layer over the hydrophilic foam and/or a bottom film layer under the hydrophilic foam. The film layer(s) may comprise polyurethane, polyethylene, polytetrafluoroethylene, or blends thereof. In certain embodiments, the film layer(s) cover at least part of a side wall of the drainage layer. In certain embodiments, the hydrophilic foam is sandwiched between a top film layer and a bottom film layer. The film layers may be at least partially welded together at the edges. In certain embodiments, the film layers are at least spot-welded, thereby creating fluid channels. In certain embodiments, the film layers may cover less than 100%, 90%, 70%, 50%, 30%, or 10% of the surface area of the bottom surface and/or the top surface of the hydrophilic foam. The uncovered portion of the hydrophilic foam layer may have asterisk shape, spiral shape, cross-hatch shape, starfish shape, or lobe shape. In certain embodiments, the hydrophilic foam is fully encased by the film layer.

In certain embodiments, the drainage layer is provided with a thickness less than its width and length, wherein the drainage layer further comprises at least one cut extending through at least a portion of the thickness of the drainage layer to define a section detachable from the drainage layer to permit the drainage layer to be sized in a dimensionally-independent manner wherein the length and the width of the drainage layer can be modified independently of each other. The system may further comprise an organ protection layer. The system may further comprise a port attachable to an aperture formed in the drape and the conduit.

Certain embodiments of the invention are directed to improved methods of treating abdominal wounds or incisions with negative pressure. For example and for illustrative purposes only, in certain embodiments, a method of treating a wound site using negative pressure, comprises: placing a hydrophilic drainage layer onto the wound site; placing a porous pad over the hydrophilic drainage layer; sealing the wound site with a flexible drape configured to be positioned over the wound and sealed to the skin surrounding the wound; and applying negative pressure to the wound site from a source of negative pressure, wherein the source of negative pressure is applied through a conduit fluidically connected between the drape and the source of negative pressure. The hydrophilic drainage layer may comprise a polyvinyl alcohol (PVA) foam. In some embodiments, the hydrophilic drainage layer comprises an organic protection layer pre-attached to a hydrophilic foam. In certain embodiments, the side wall of the hydrophilic drainage layer touches onto the wound site.

Certain embodiments of the invention are directed to improved methods of treating abdominal wounds or incisions with negative pressure. For example and for illustrative purposes only, some embodiments employ a porous pad with detachable or cuttable sections permitting desired sizing of the pad to the wound site. Sizing of the foam pad may in some embodiments be performed in a dimensionally-independent manner so that, for example, the width and/or length may be modified independently of each other. Further embodiments also provide for an organ protection layer to be placed in contact with the wound site, where the organ protection layer is preferably minimally or non-adherent to the wound site and provided with slits or other openings for the removal of wound exudate or fluids and the application of negative pressure to the wound site.

Certain embodiments provide for a negative pressure treatment system comprising an organ protection layer placed over the wound, a porous pad configured to be sized and positioned over the organ protection layer, a flexible drape configured to be placed above the wound and sealed to the skin surrounding the wound, and which further comprises a conduit configured to deliver negative pressure to the wound through an aperture in the flexible drape and through the porous pad and organ protection layer.

In a preferred embodiment, a porous pad is provided for the treatment of wounds with negative pressure, wherein the porous pad is comprised of a porous material suitable for channeling wound exudate from a wound site to a source of negative pressure. The porous pad preferably comprises a generally planar shape with a thickness less than its width and length, and preferably comprises at least one cut extending through a least a portion of the thickness of the pad, whereby the cut defines a pad section detachable from the remainder of the pad so as to permit modification of the size of the pad (for example its length and/or width). In certain embodiments, the cuts may be comprised of arcuate and/or elliptical cuts, and may further comprise additional inner and outer cuts. In further embodiments, additional intermediate cuts may also be present.

In another preferred embodiment, a system for the treatment of a wound site comprises a organ protection layer provided with openings for channeling wound exudate and distributing negative pressure, a generally planar porous pad suitable for transmitting negative pressure to a wound site and comprising at least one cut extending through a portion of the pad's thickness so as to define a detachable pad, a flexible drape, a conduit, and a source of negative pressure configured to deliver negative pressure through the conduit to the wound site.

In yet another preferred embodiment, a method of treating a wound site using negative pressure may comprise placing an organ protection layer onto the wound site; placing a porous pad over the organ protection layer, where the porous pad is perforated to allow removal of pad portions so as to permit sizing of the pad in a dimensionally-independent manner to fit the wound site; sealing the wound site with a flexible drape configured to be positioned over the wound and sealed to the skin surrounding the wound; connecting a source of negative pressure to the wound site; and maintaining the application of negative pressure until the wound site has healed appropriately.

It should be understood by those skilled in the art that hydrophilic material or hydrophilic foam in embodiments described in this section or elsewhere in this application can be substituted for other materials or structures having similar fluid-drawing ability, such as an acquisition distribution material, DryWeb TDL2, SlimCore TL4, or the like.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

Embodiments of the present disclosure will now be described hereinafter, by way of example only, with reference to the accompanying drawings in which.

DETAILED DESCRIPTION

Preferred embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using reduced pressure. Wounds and/or wound sites include, but are not limited to, open wounds, pressure sores, ulcers and burns. Open wounds and/or wound sites may also include incisions (e.g., abdominal incisions) or other openings, tears, or fistulas, for example, in the abdominal or peritoneal cavity. Treatment of such wounds can be performed using negative pressure wound therapy, wherein a reduced or negative pressure can be applied to the wound to facilitate and promote healing of the wound. It will also be appreciated that the negative pressure systems and methods as disclosed herein may be applied to other parts of the body, and are not necessarily limited to treatment of wounds.

Figure 1:
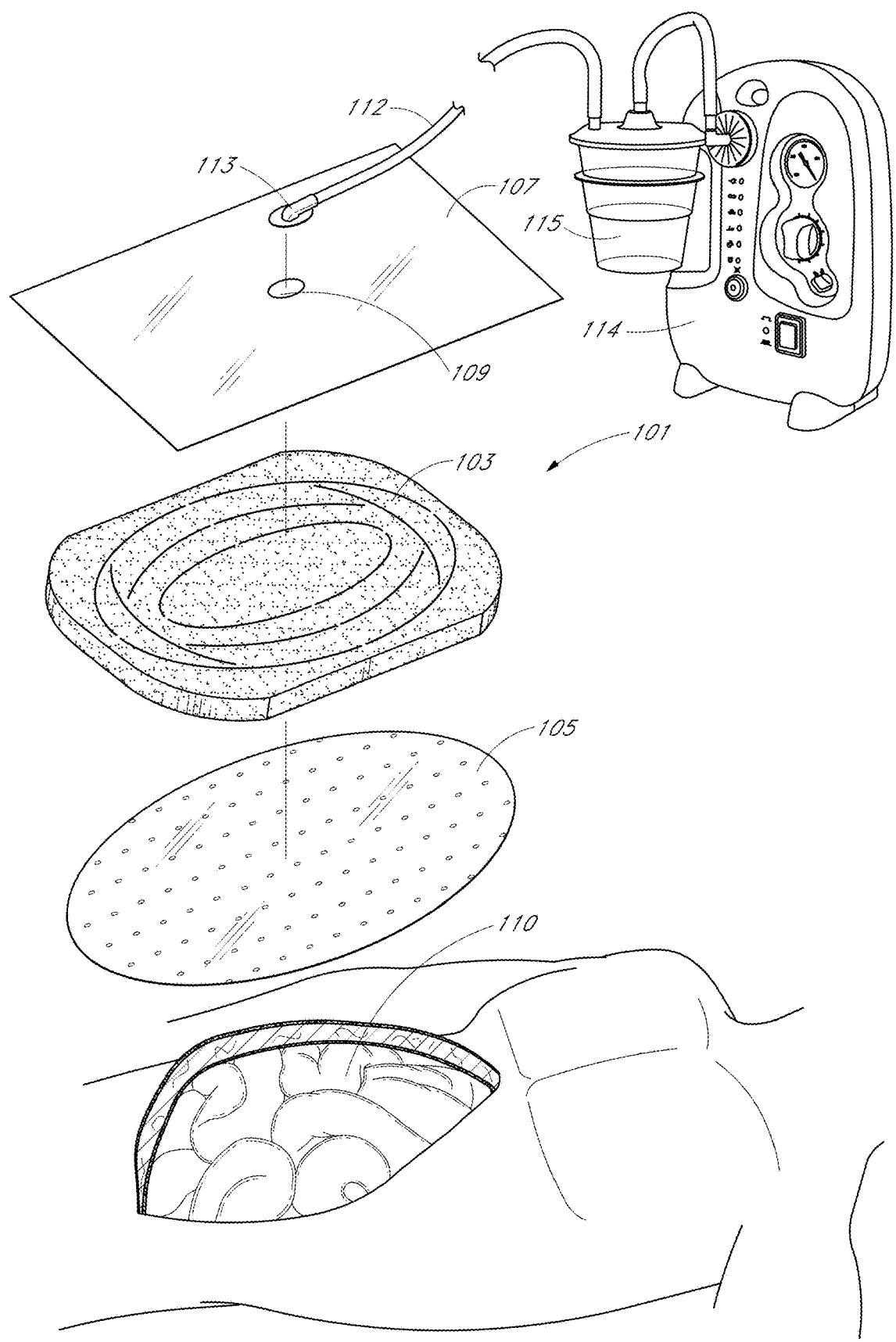
FIG. 1 is a schematic illustration of a system for the treatment of abdominal wounds.
Figure 2:
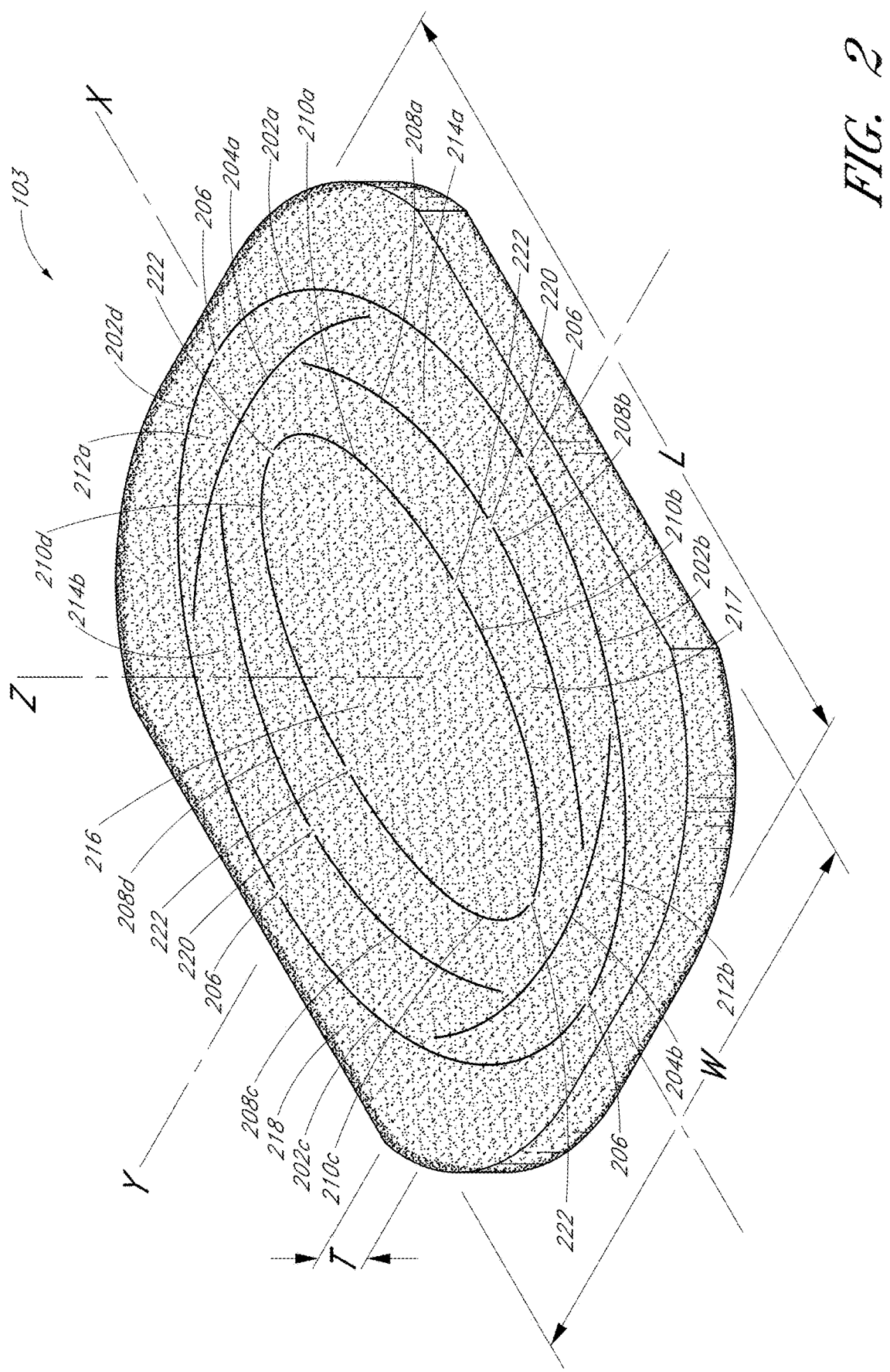
FIG. 2 illustrates a perspective view of one embodiment of a porous pad that can be used in the treatment of wounds.

Turning to FIG. 1, treatment of a wound with negative pressure in certain embodiments uses a negative pressure treatment system 101 as illustrated schematically here. In this embodiment, a wound site 110, illustrated here as an abdominal wound site, may benefit from treatment with negative pressure. Such abdominal wound sites may be a result of, for example, an accident or due to surgical intervention. In some cases, medical conditions such as abdominal compartment syndrome, abdominal hypertension, sepsis, or fluid edema may require decompression of the abdomen with a surgical incision through the abdominal wall to expose the peritoneal space, after which the opening may need to be maintained in an open, accessible state until the condition resolves. Other conditions may also necessitate that an opening—particularly in the abdominal cavity—remain open, for example if multiple surgical procedures are required (possibly incidental to trauma), or there is evidence of clinical conditions such as peritonitis or necrotizing fasciitis.

In cases where there is a wound, particularly in the abdomen, management of possible complications relating to the exposure of organs and the peritoneal space is desired, whether or not the wound is to remain open or if it will be closed. Therapy, preferably using the application of negative pressure, can be targeted to minimize the risk of infection, while promoting tissue viability and the removal of deleterious substances from the wound site. The application of reduced or negative pressure to a wound site has been found to generally promote faster healing, increased blood flow, decreased bacterial burden, increased rate of granulation tissue formation, to stimulate the proliferation of fibroblasts, stimulate the proliferation of endothelial cells, close chronic open wounds, inhibit burn penetration, and/or enhance flap and graft attachment, among other things. It has also been reported that wounds that have exhibited positive response to treatment by the application of negative pressure include infected open wounds, decubitus ulcers, dehisced incisions, partial thickness burns, and various lesions to which flaps or grafts have been attached. Consequently, the application of negative pressure to a wound site 110 can be beneficial to a patient.

Accordingly, certain embodiments provide for an organ protection layer 105 to be placed over the wound site 110. Preferably, the organ protection layer 105 can be a thin, flexible material which will not adhere to the wound site or the exposed viscera in close proximity. For example, polymers such as polyurethane, polyethylene, polytetrafluoroethylene, or blends thereof may be used. In one embodiment, the organ protection layer is permeable. For example, the organ protection layer 105 can be provided with openings, such as holes, slits, or channels, to allow the removal of fluids from the wound site 110 or the transmittal of negative pressure to the wound site 110. Additional embodiments of the organ protection layer 105 are described in further detail below.

Certain embodiments of the negative pressure treatment system 101 may also use a porous pad 103, which can be disposed over the organ protection layer 105. This pad 103 can be constructed from a porous material, for example foam, that is soft, resiliently flexible, and generally conformable to the wound site 110. Such a foam can include an open-celled and reticulated foam made, for example, of a polymer. Suitable foams include foams composed of, for example, polyurethane, silicone, and polyvinyl alcohol. Preferably, this pad 103 can channel wound exudate and other fluids through itself when negative pressure is applied to the wound. Some pads 103 may include preformed channels or openings for such purposes. In certain embodiments, the pad 103 may have a thickness between about one inch and about two inches. The pad may also have a length of between about 16 and 17 inches, and a width of between about 11 and 12 inches. In other embodiments, the thickness, width, and/or length can have other suitable values. Other aspects of the pad 103 are discussed in further detail below.

Preferably, a drape 107 is used to seal the wound site 110. The drape 107 can be at least partially liquid impermeable, such that at least a partial negative pressure may be maintained at the wound site. Suitable materials for the drape 107 include, without limitation, synthetic polymeric materials that do not significantly absorb aqueous fluids, including polyolefins such as polyethylene and polypropylene, polyurethanes, polysiloxanes, polyamides, polyesters, and other copolymers and mixtures thereof. The materials used in the drape may be hydrophobic or hydrophilic. Examples of suitable materials include Transeal® available from DeRoyal and OpSite® available from Smith & Nephew. In order to aid patient comfort and avoid skin maceration, the drapes in certain embodiments are at least partly breathable, such that water vapor is able to pass through without remaining trapped under the dressing. An adhesive layer may be provided on at least a portion the underside of the drape 107 to secure the drape to the skin of the patient, although certain embodiments may instead use a separate adhesive or adhesive strip. Optionally, a release layer may be disposed over the adhesive layer to protect it prior to use and to facilitate handling the drape 107; in some embodiments, the release layer may be composed of multiple sections.

The negative pressure system 101 can be connected to a source of negative pressure, for example a pump 114. One example of a suitable pump is the Renasys EZ pump available from Smith & Nephew. The drape 107 may be connected to the source of negative pressure 114 via a conduit 112. The conduit 112 may be connected to a port 113 situated over an aperture 109 in the drape 107, or else the conduit 112 may be connected directly through the aperture 109 without the use of a port. In a further alternative, the conduit may pass underneath the drape and extend from a side of the drape. U.S. Pat. No. 8,791,315, "SYSTEMS AND METHODS FOR USING NEGATIVE PRESSURE WOUND THERAPY TO MANAGE OPEN ABDOMINAL WOUNDS," issued Jul. 29, 2014 and U.S. Pat. No. 7,524,315, "APPARATUS FOR ASPIRING, IRRIGATING AND CLEANSING WOUNDS," issued Apr. 28, 2009 disclose other similar aspects of negative pressure systems and is hereby incorporated by reference in its entirety and should be considered a part of this application. Additional applications referenced herein this application are also hereby incorporated by reference in their entireties as if fully set forth herein.

In many applications, a container or other storage unit 115 may be interposed between the source of negative pressure 114 and the conduit 112 so as to permit wound exudate and other fluids removed from the wound site to be stored without entering the source of negative pressure. Certain types of negative pressure sources—for example, peristaltic pumps—may also permit a container 115 to be placed after the pump 114. Some embodiments may also use a filter to prevent fluids, aerosols, and other microbial contaminants from leaving the container 115 and/or entering the source of negative pressure 114. Further embodiments may also include a shut-off valve or occluding hydrophobic and/or oleophobic filter in the container to prevent overflow; other embodiments may include sensing means, such as capacitive sensors or other fluid level detectors that act to stop or shut off the source of negative pressure should the level of fluid in the container be nearing capacity. At the pump exhaust, it may also be preferable to provide an odor filter, such as an activated charcoal canister.

Figure 3:
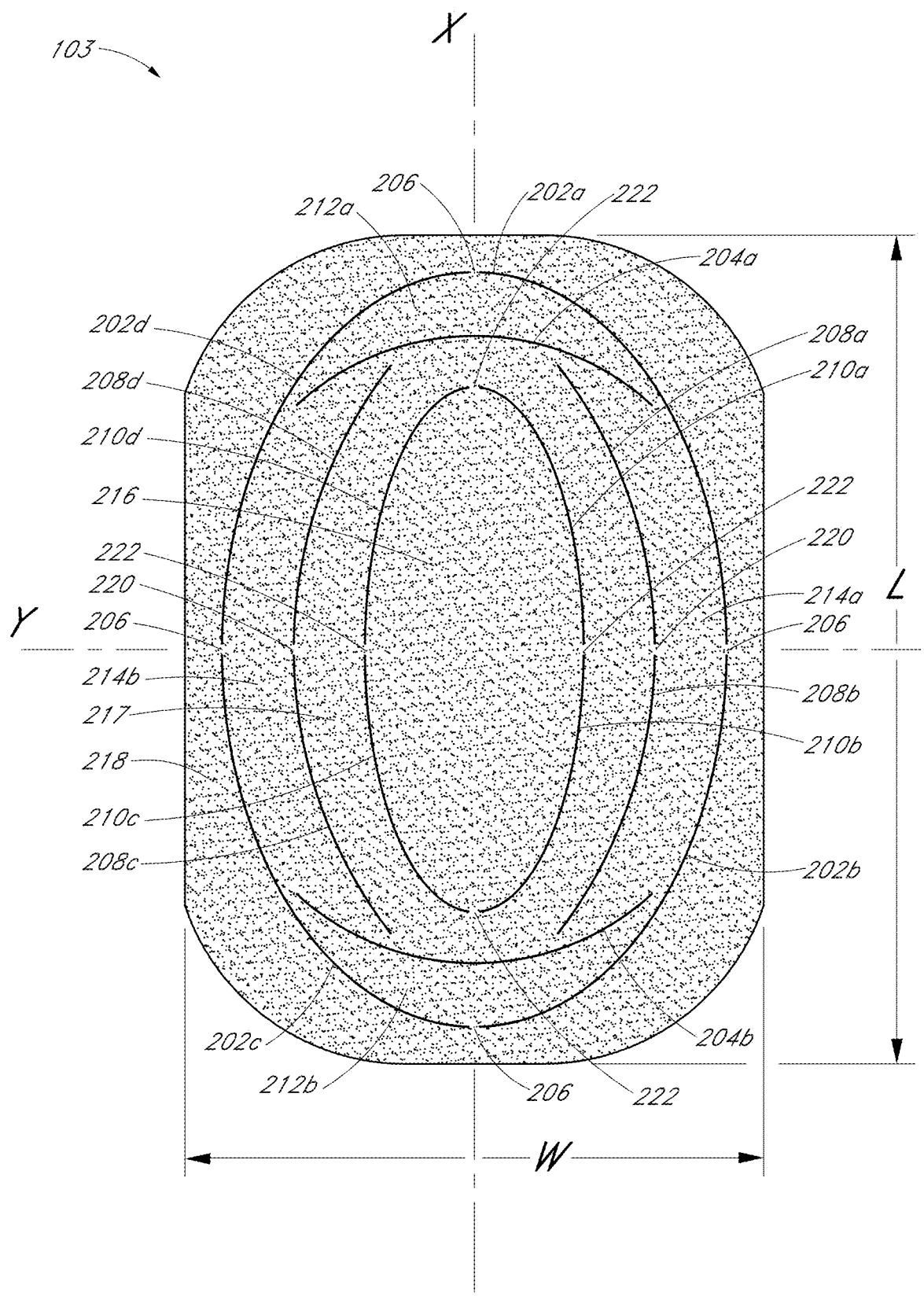
FIG. 3 illustrates a top view of the same porous pad.
Figure 4:
FIGS. 4-5 illustrate side views of the same porous pad.
Figure 5:
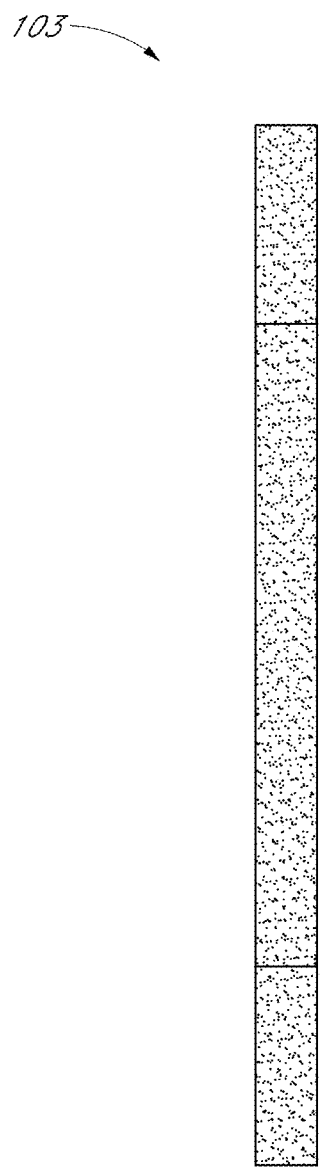
Figure 6:
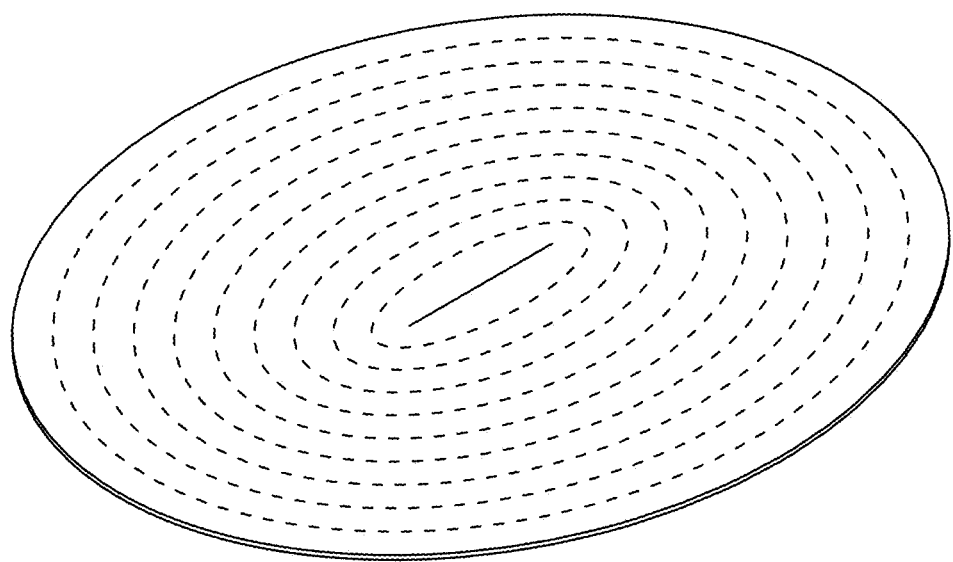
FIGS. 6-56 illustrate views of different embodiments of an organ protection layer.
Figure 7:
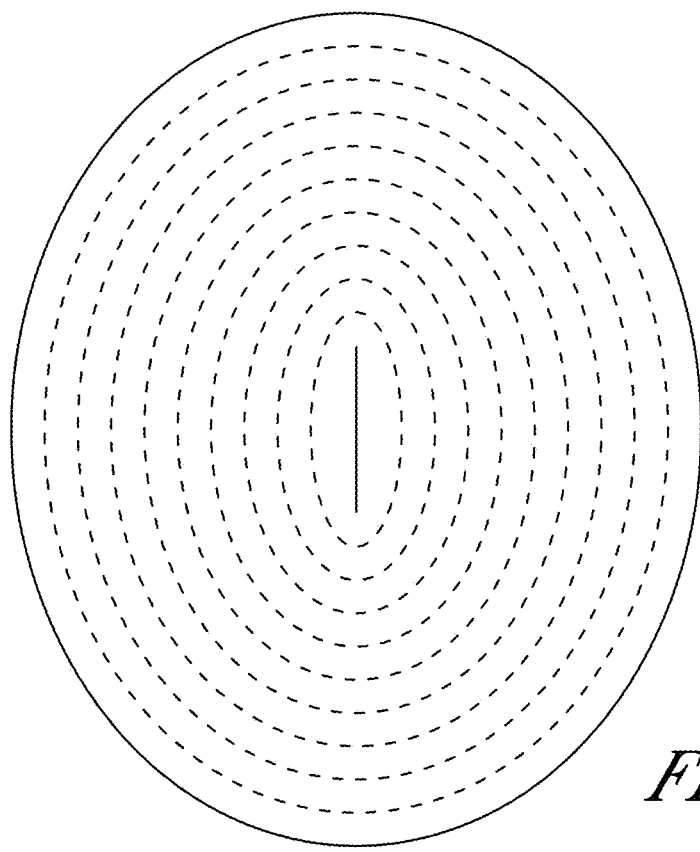
Figure 8:
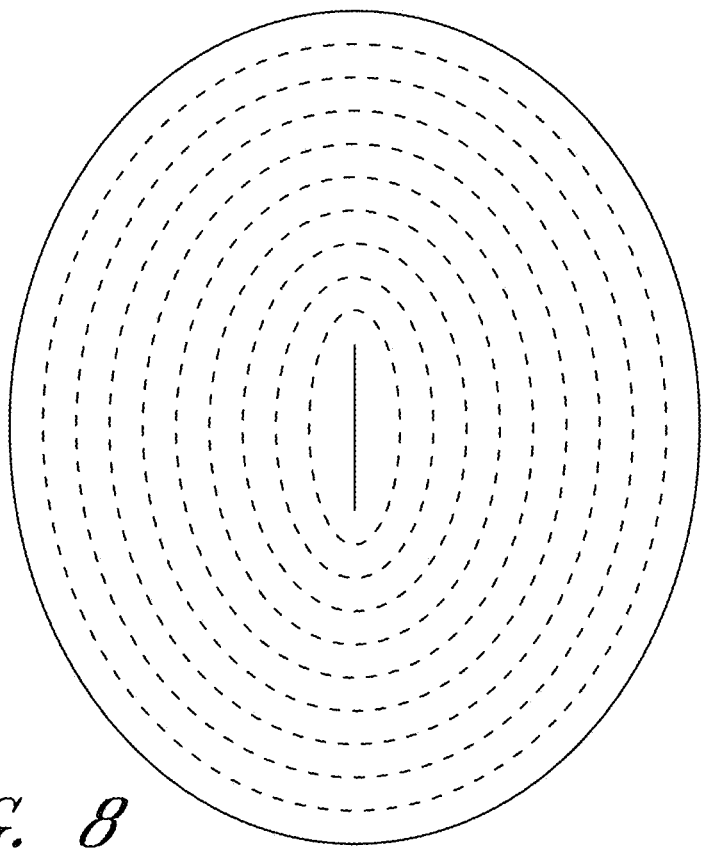
Figure 9:
Figure 10:
Figure 11:
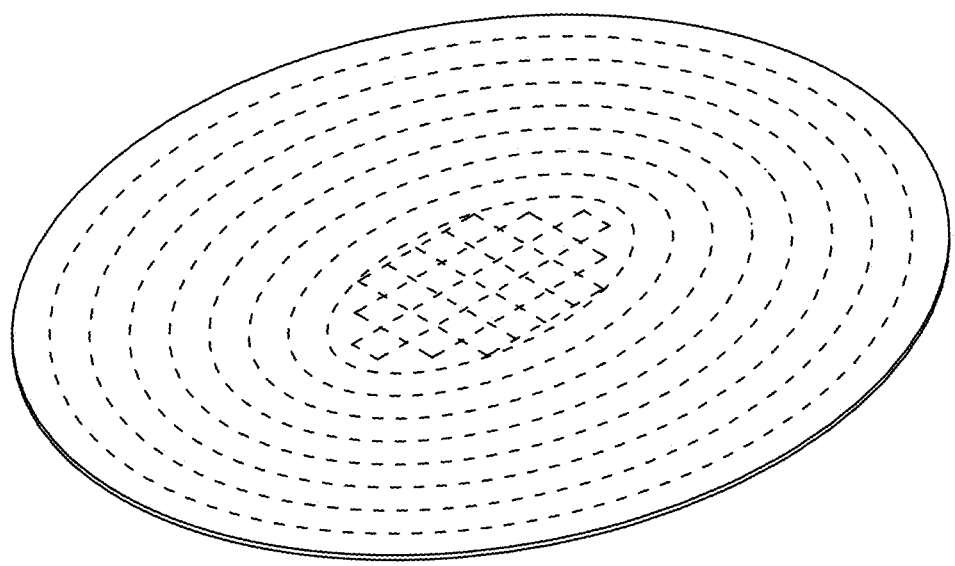
Figure 12:
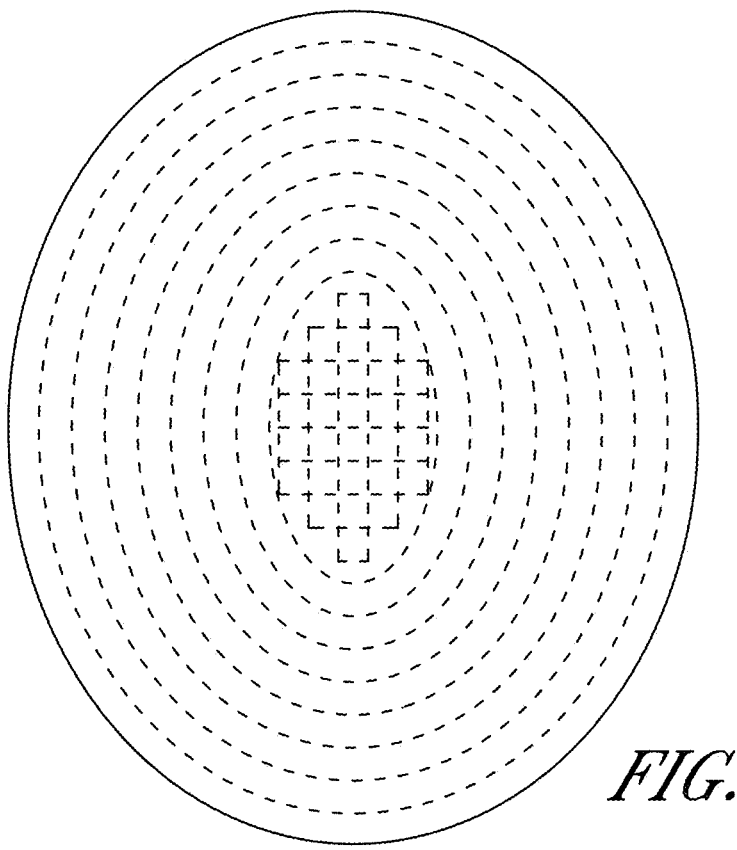
Figure 13:
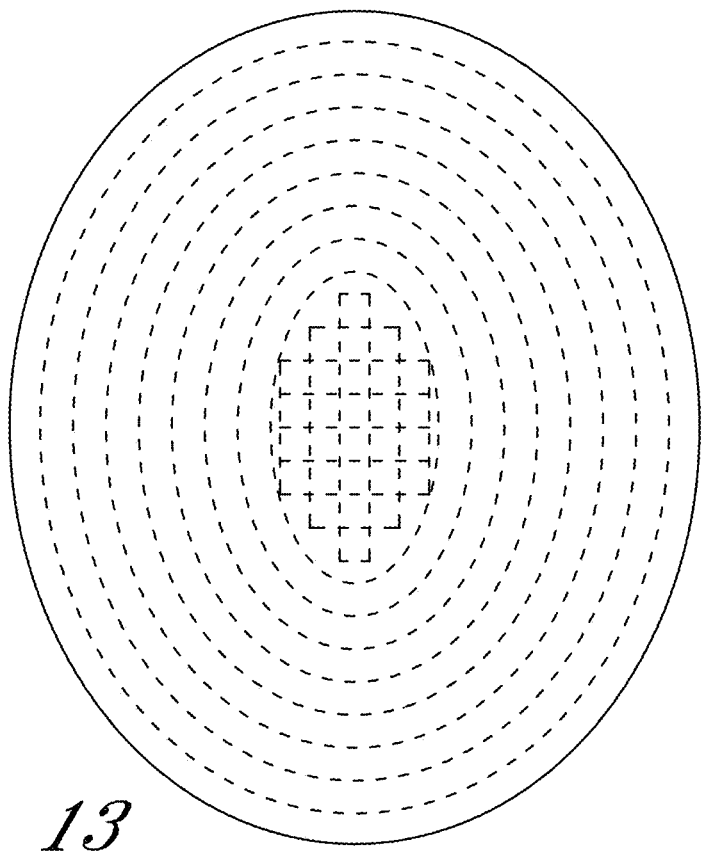
Figure 14:
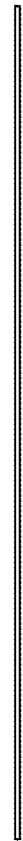
Figure 15:
Figure 16:
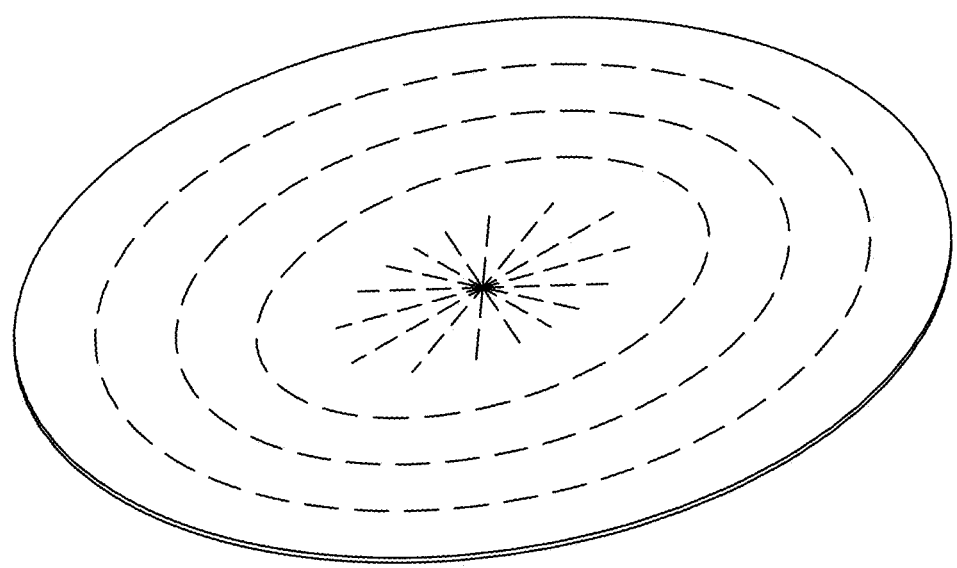
Figure 17:
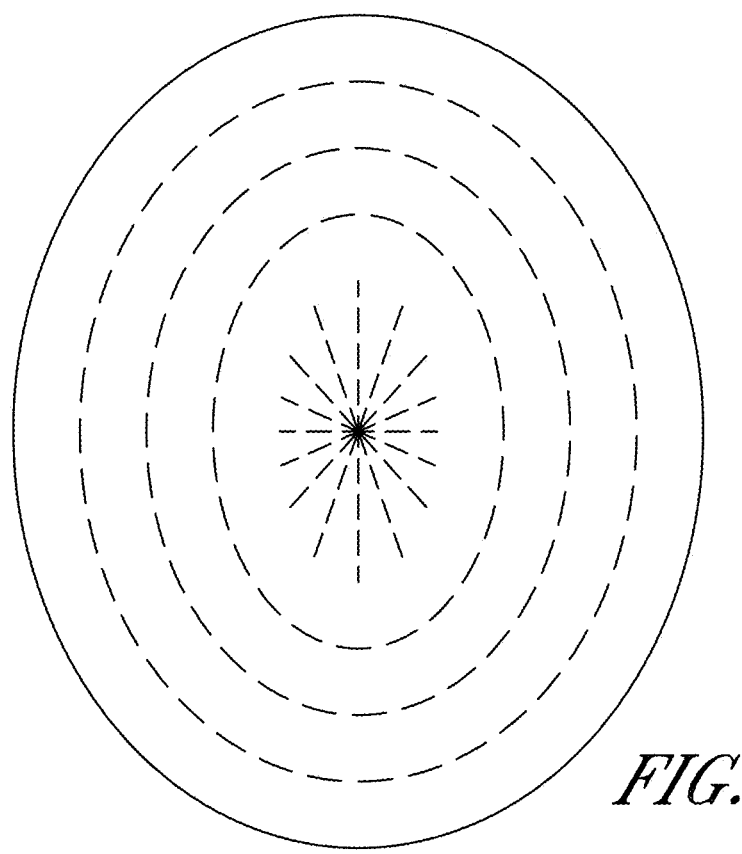
Figure 18:
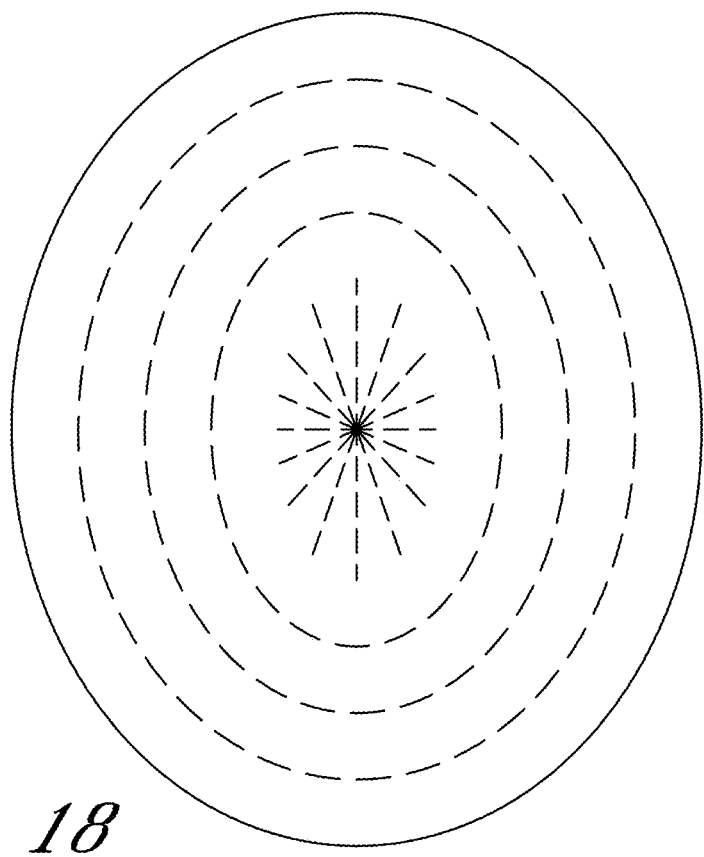
Figure 19:
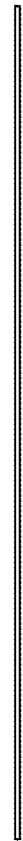
Figure 20:
Figure 21:
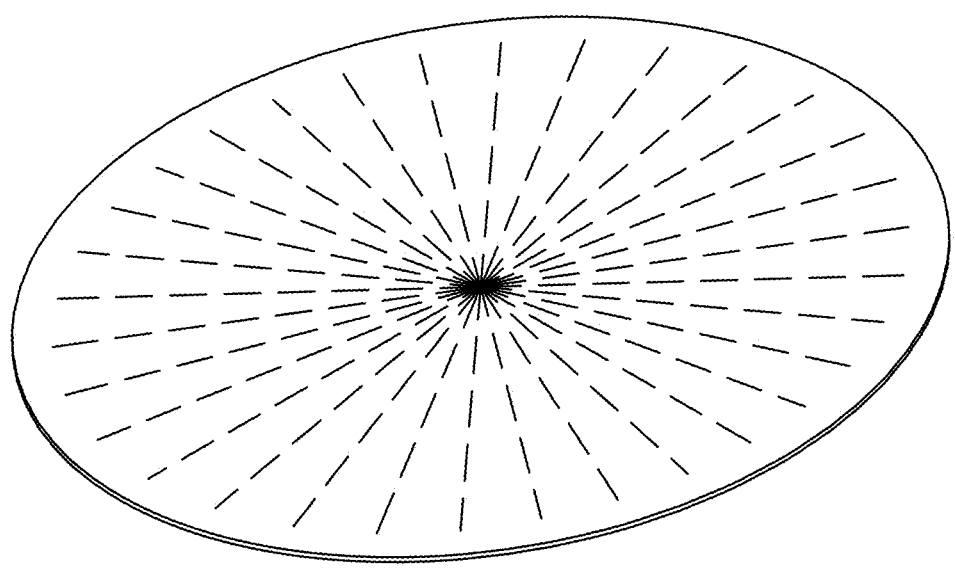
Figure 22:
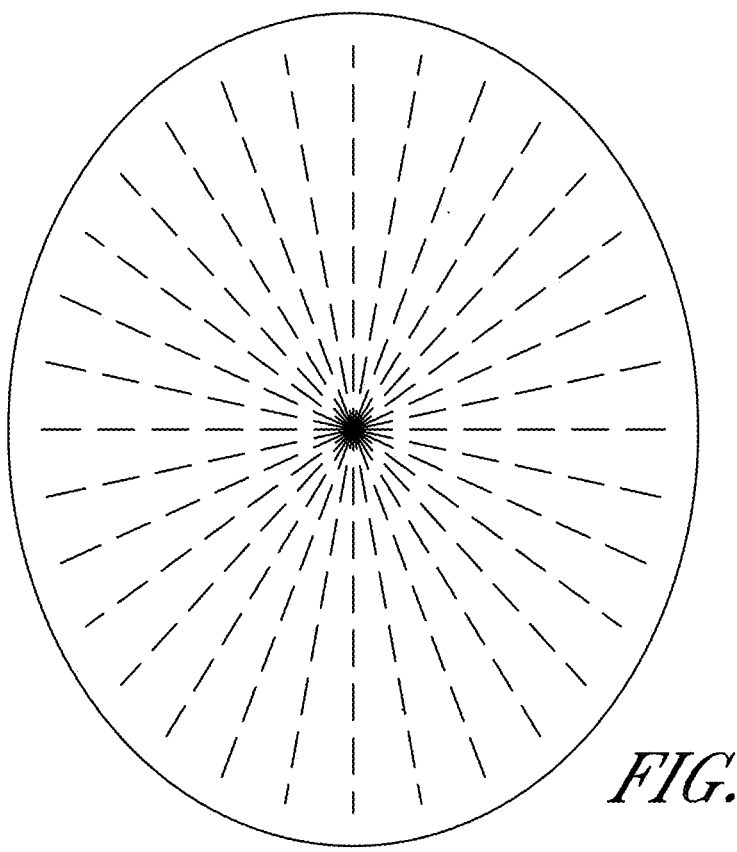
Figure 23:
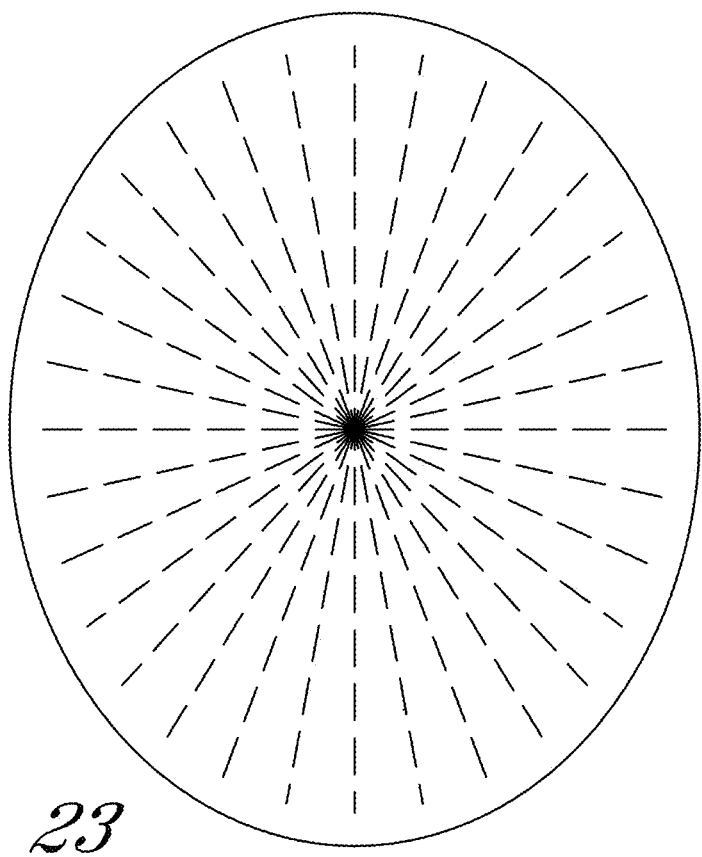
Figure 24:
Figure 25:
Figure 26:
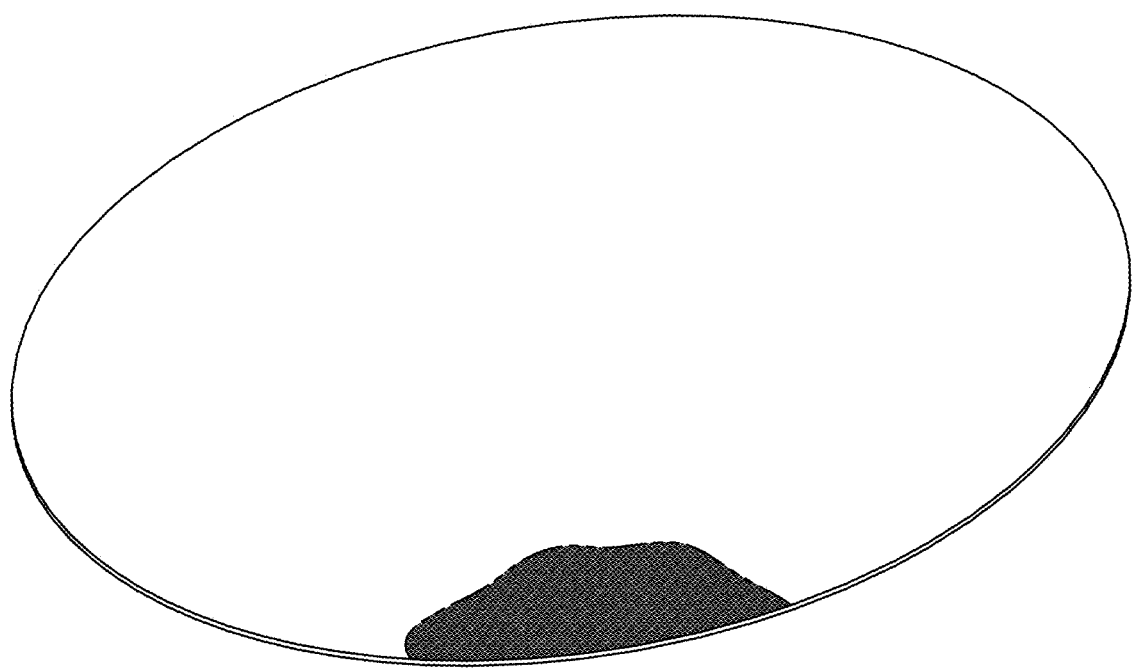
Figure 27:
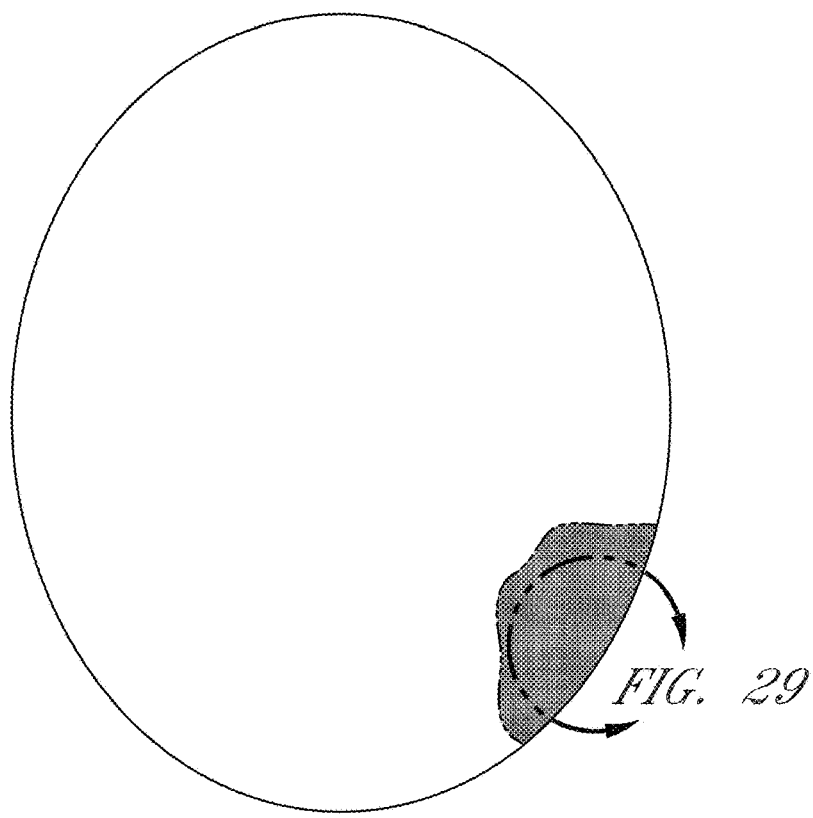
Figure 28:
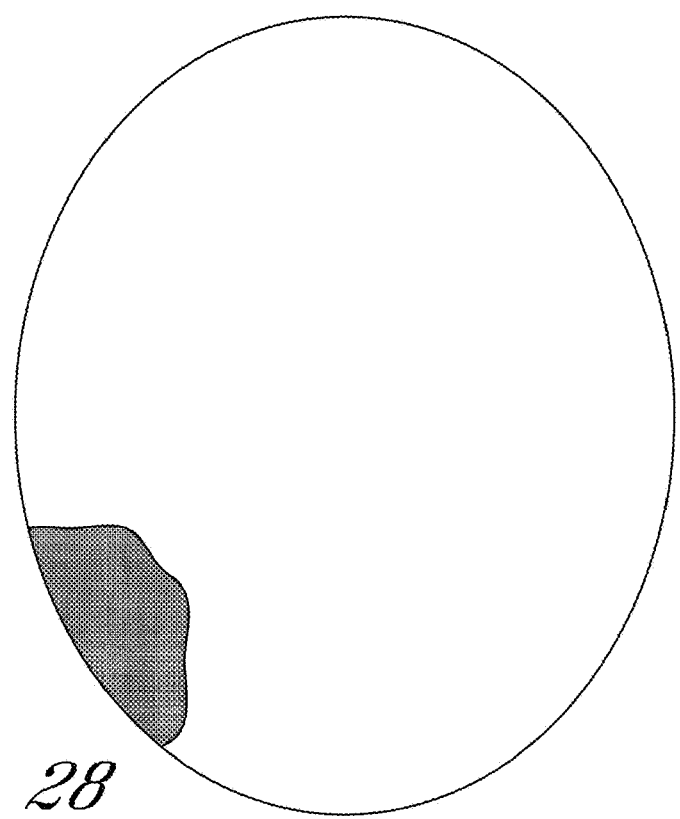
Figure 29:
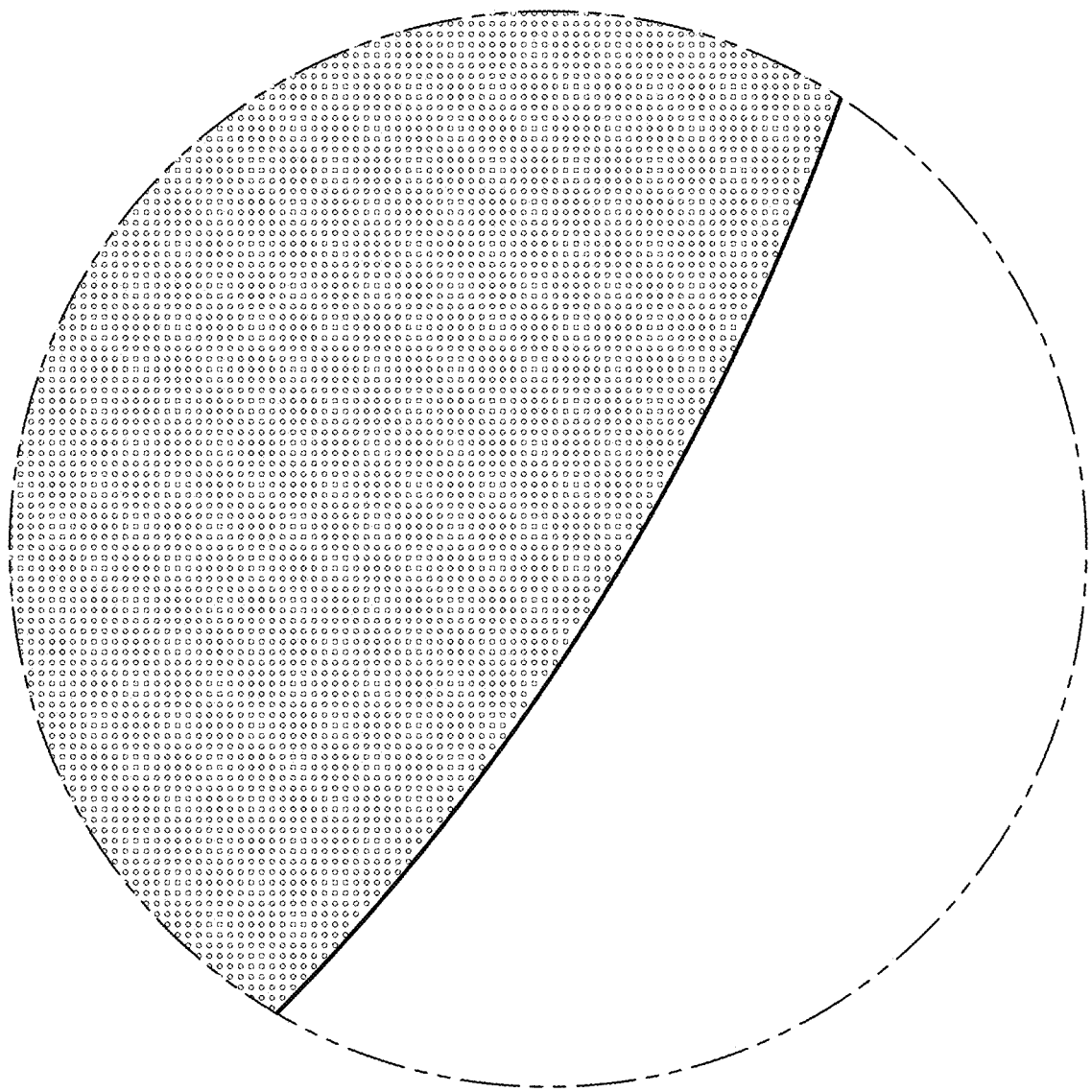
Figure 30:
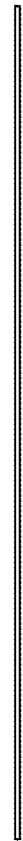
Figure 31:
Figure 32:
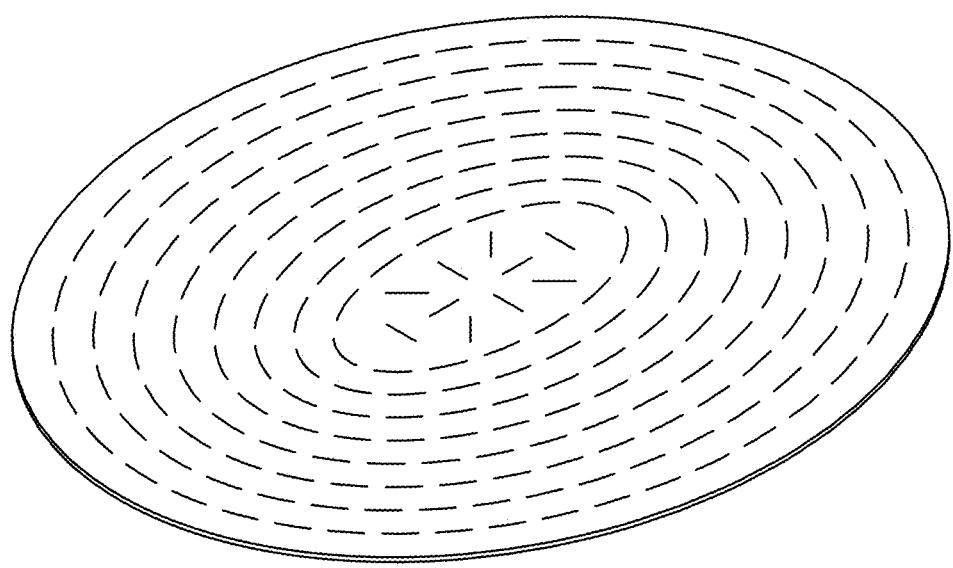
Figure 33:
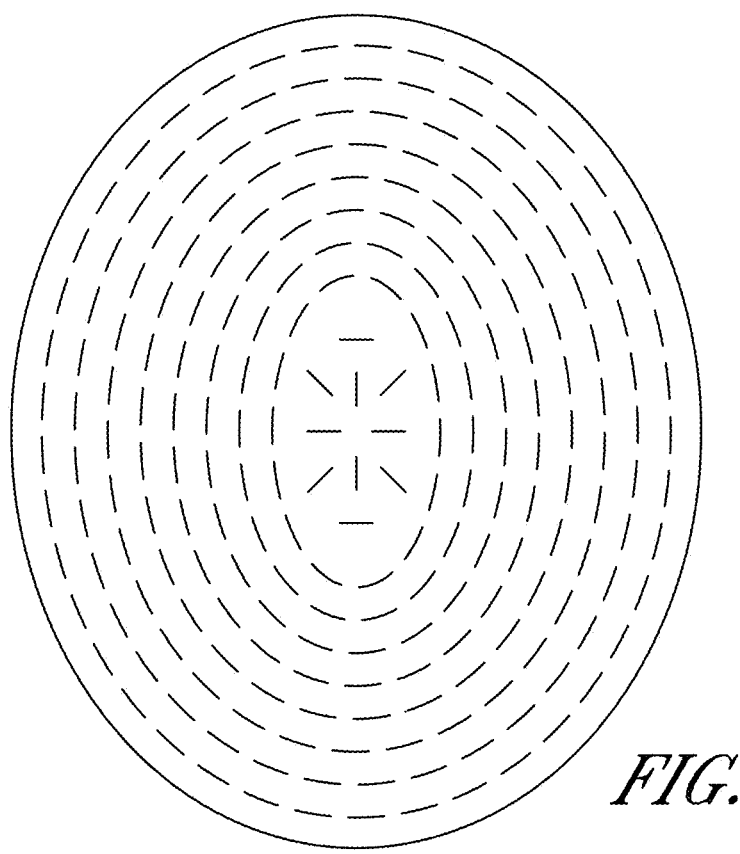
Figure 34:
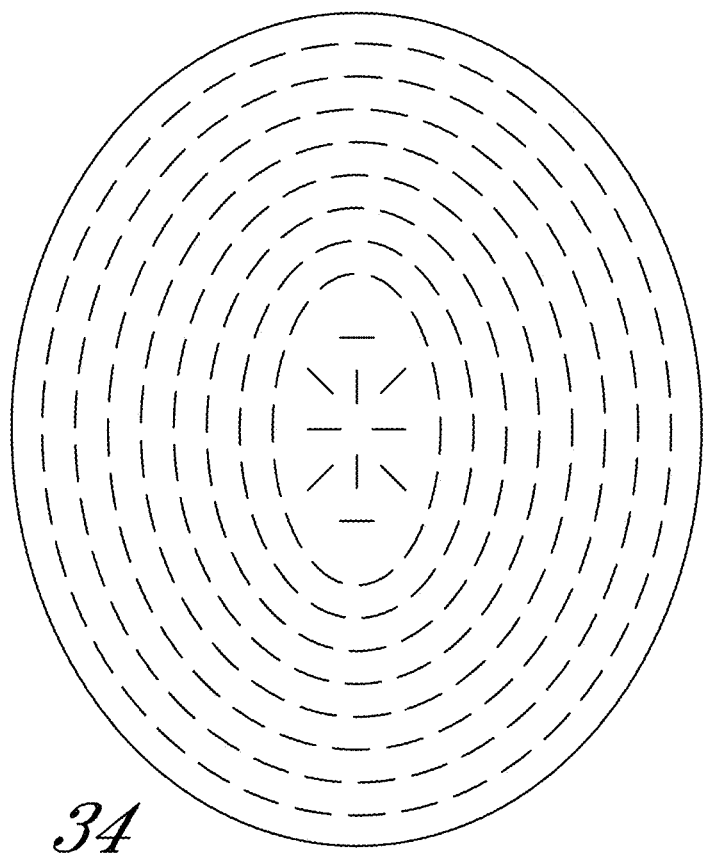
Figure 35:
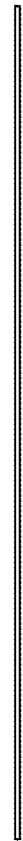
Figure 36:
Figure 37:
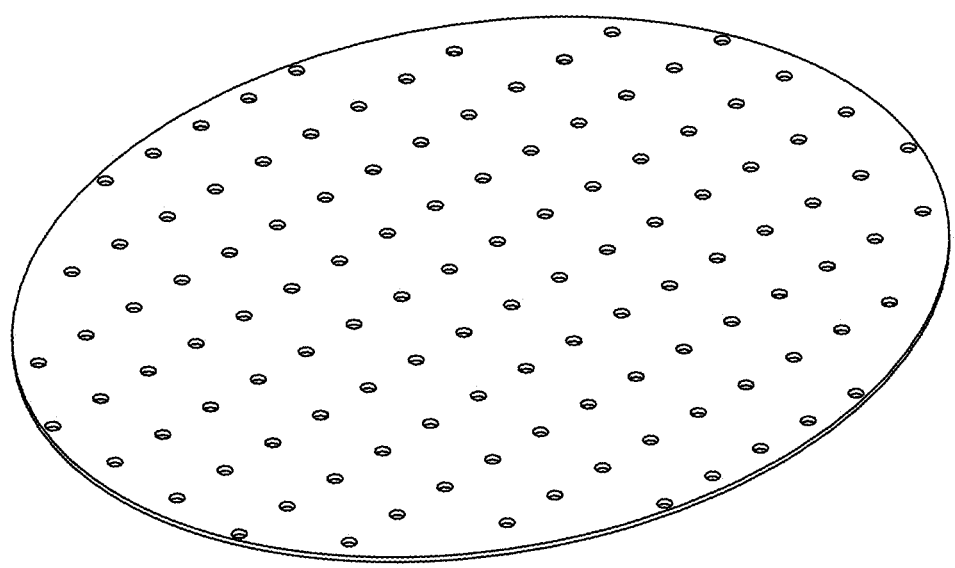
Figure 38:
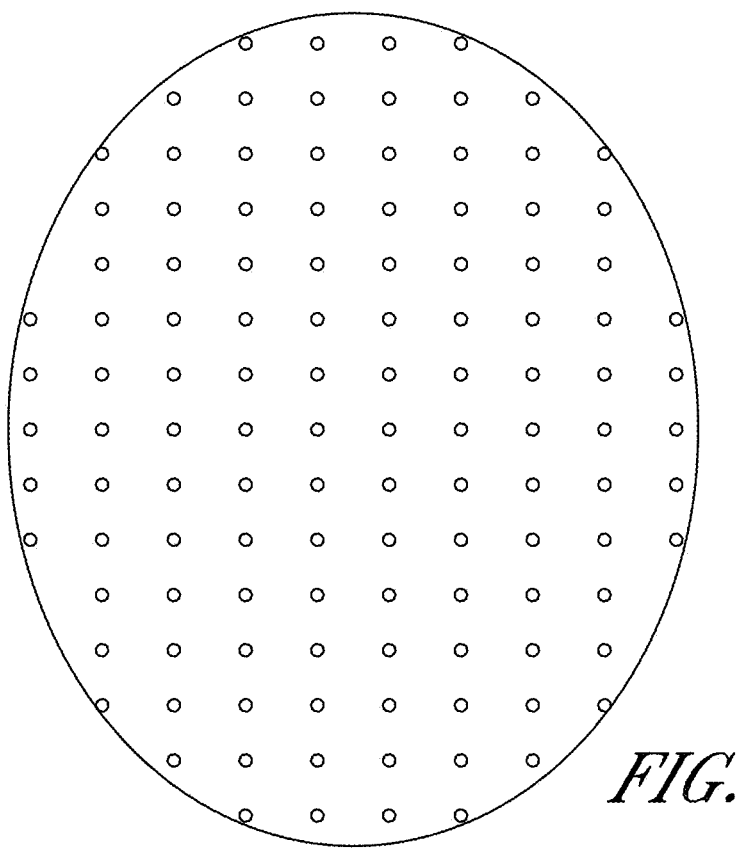
Figure 39:
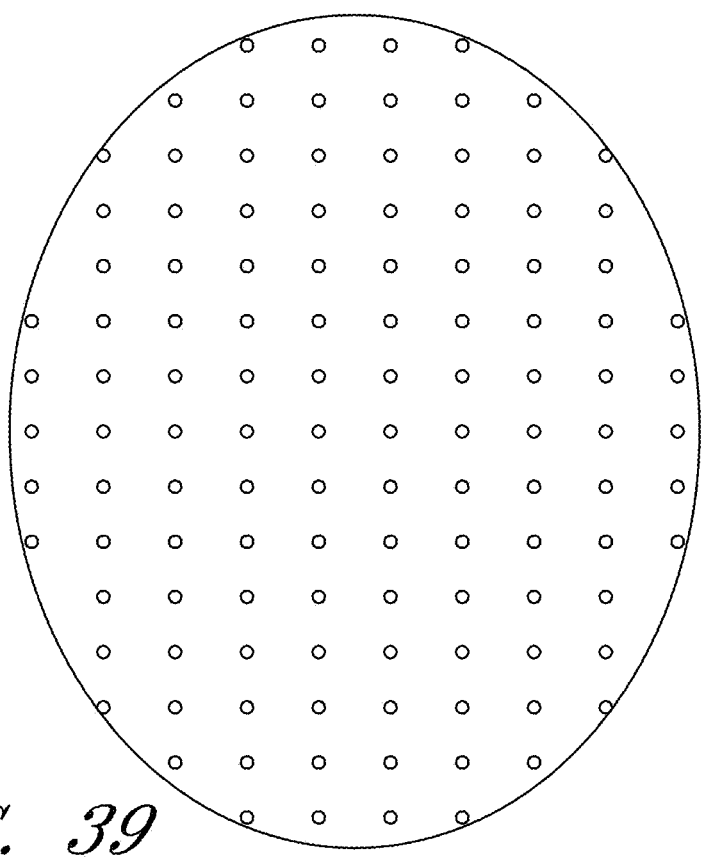
Figure 40:
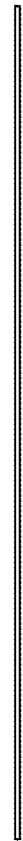
Figure 41:
Figure 42:
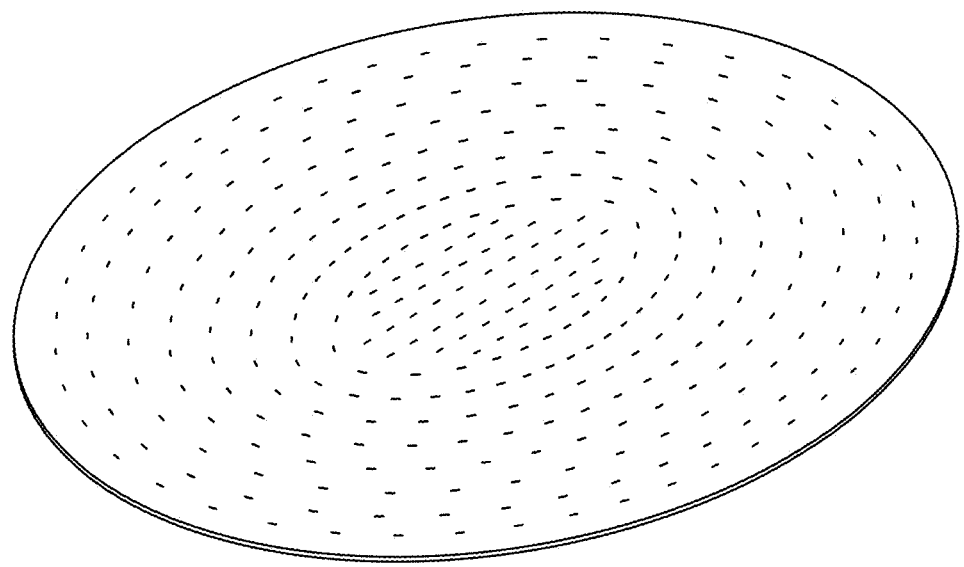
Figure 43:
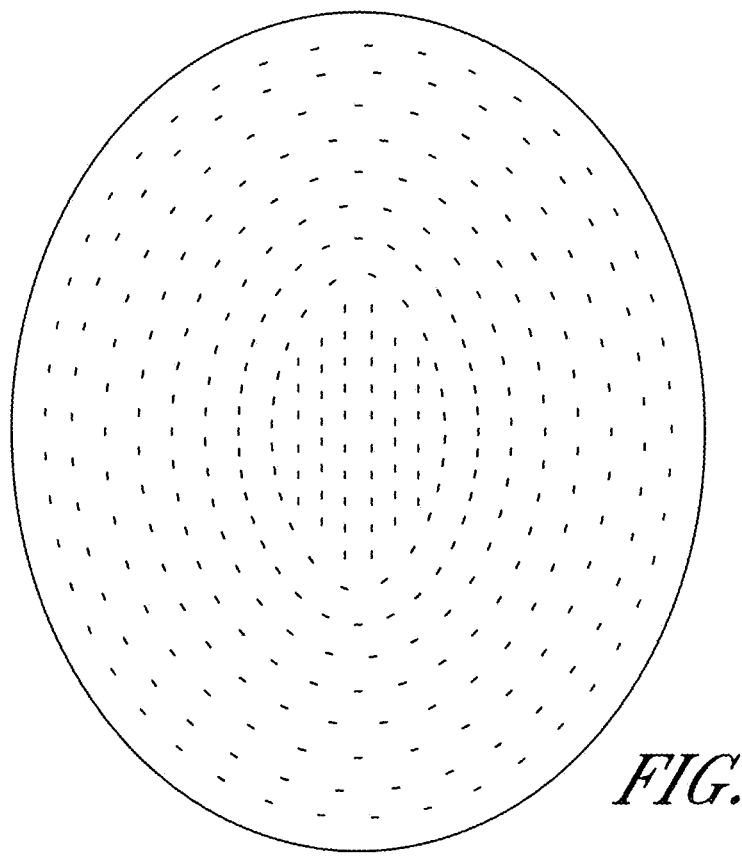
Figure 44:
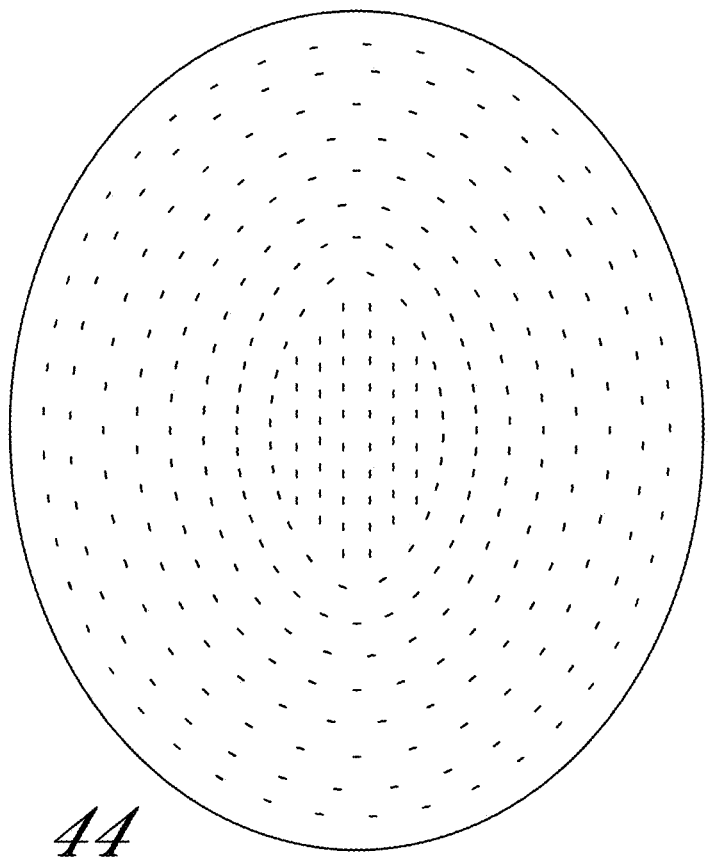
Figure 45:
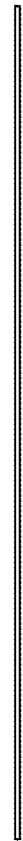
Figure 46:
Figure 47:
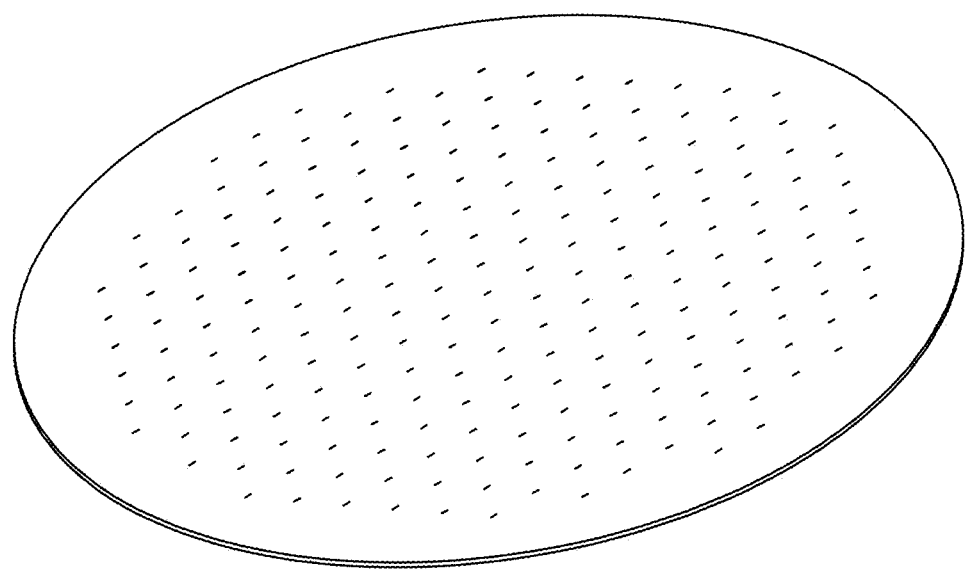
Figure 48:
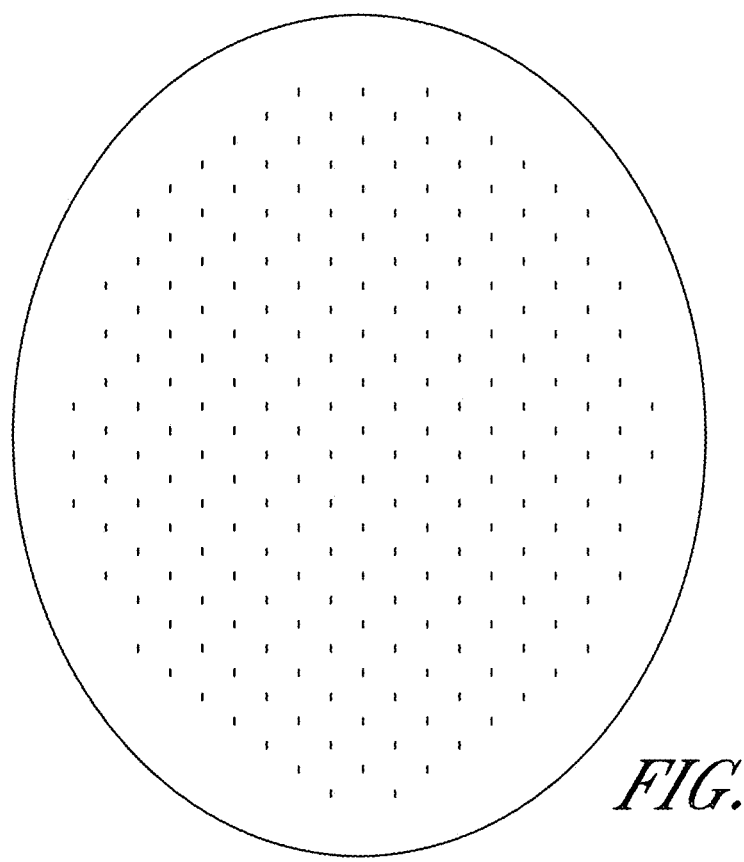
Figure 49:
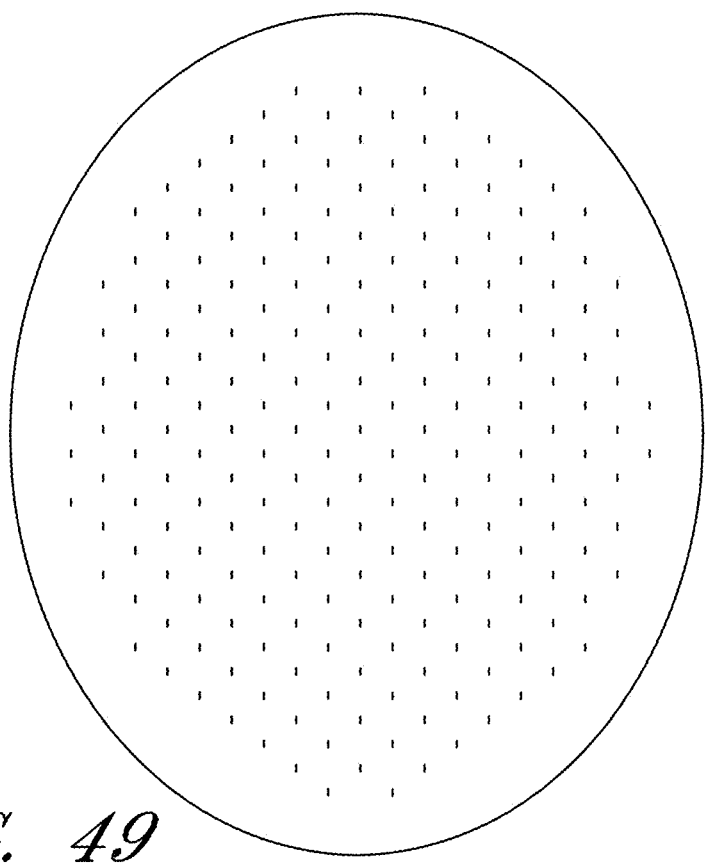
Figure 50:
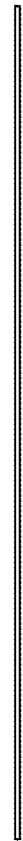
Figure 51:
Figure 52:
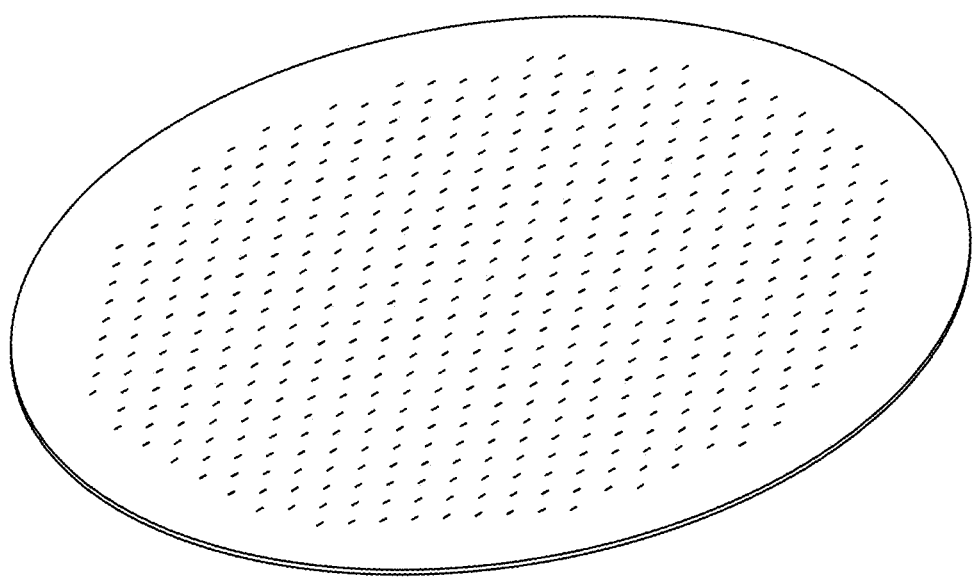
Figure 53:
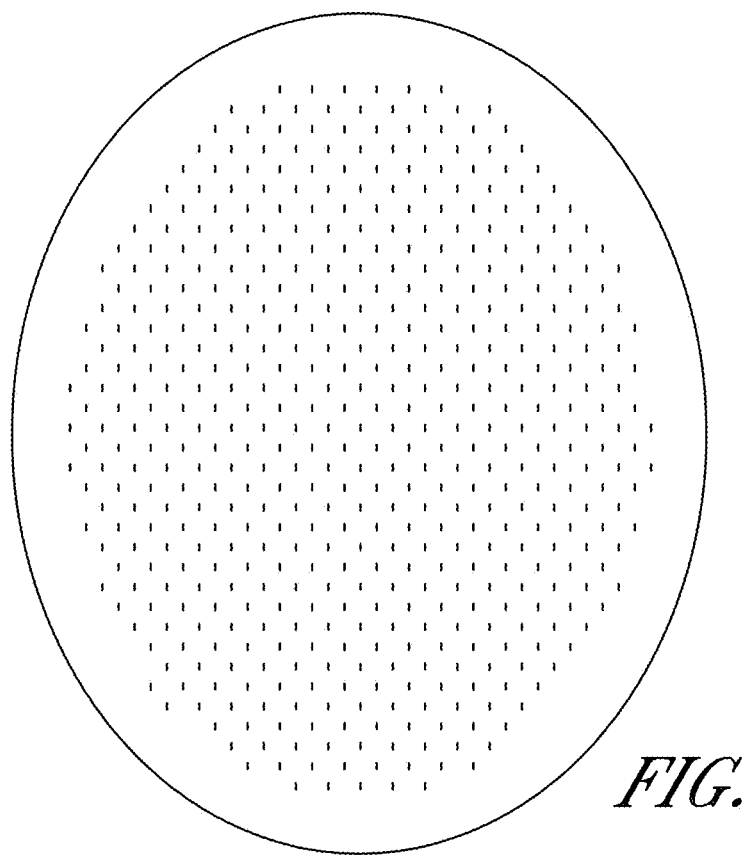
Figure 54:
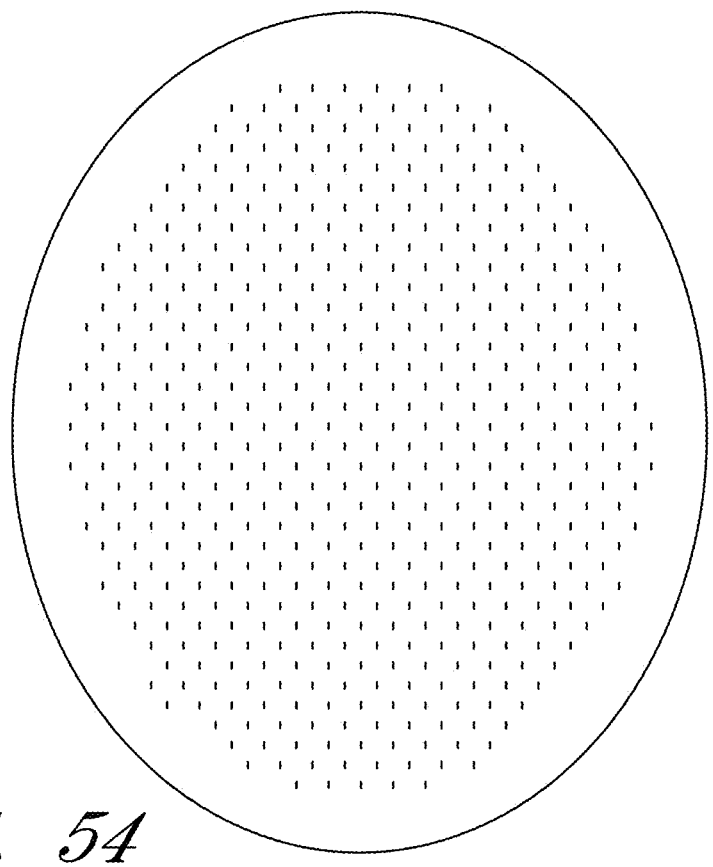
Figure 55:
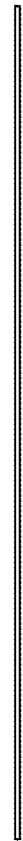
Figure 56:

With reference to FIGS. 3-5, perspective and top views of an embodiment of the porous pad 103 are shown. The pad 103 preferably has one or more perforations made thereon, illustrated for example at arcuate cuts 202, 204, 208, and 210. These cuts may be formed on the pad 103 using any suitable mechanism, including, for example but without, limitation cutting blades, die cutting, or hot wire cutting, and these cuts preferably extend through at least portion of the thickness of the pad 103. The cuts do not need to be continuous, and may consist, for example, of multiple small perforations. In one embodiment, perforations extend entirely across the thickness of the pad 103. In order to ensure that the pad 103 remains structurally intact during handling and use, the cuts made through the pad 103 preferably retain one or more small bridge portions, such as the bridge portion 206.

In one embodiment, the pad 103 has a substantially rectangular shape having a length L, a width W, and a thickness T defined about a major axis X, a minor axis Y, and a vertical axis Z, and has four rounded corners. A first series of arcuate outer cuts 202 may be formed in the pad in an elliptical shape. In the illustrated embodiment, there are four outer cuts 202*a*, 202*b*, 202*c* and 202*d*, each positioned in one of the quadrants defined by the axes X and Y, with four bridge portions 206 positioned at opposite ends along the major and minor axes. Interior to the outer cuts 202 are a series of arcuate inner cuts 210 also having an elliptical shape similarly shaped to the series of arcuate outer cuts 202. As illustrated, in one embodiment there are four inner cuts 210*a*, 210*b*, 210*c*, 210*d* also each positioned in one of the quadrants defined by the axes X and Y, with four bridge portions 222 positioned at opposite ends along the major and minor axes.

Located between the outer and inner cuts 202 and 210 are a series of intermediate cuts 204 and 208. From the top view perspective of FIG. 3, an upper arcuate cut 204*a* and a lower arcuate cut 204*b* are symmetrically arranged about minor axis Y located at opposite ends of the pad 103. Cuts 204*a* and 204*b* extend generally across the width W of the pad, symmetrically about major axis X, with these cuts 204*a*, 204*b* having a larger radius of curvature than that of the arcuate cuts 202 near the major axis X. Left and right arcuate cuts 208 are provided between the arcuate cuts 204*a*, 204*b*, extending generally length-wise across the pad. As illustrated, there may be four arcuate cuts 208*a*, 208*b*, 208*c*, 208*d*, each extending generally parallel to the portions of the arcuate cuts 202, 210 that surround them, with bridge portions 220 located on the minor axis Y. It will be appreciated that the shape and number of cuts may be varied, and that there may be more than one series of intermediate cuts between the inner and outer cuts 210, 202.

Advantageously, cuts made on the pad 103 can be used to selectively size the pad 103 to the wound site in which the pad 103 is to be placed. For example, the pad 103 can be sized by removing detachable sections from the pad 103, for example, outer section 218 that surrounds outer cuts 202, inner sections 212*a*, 212*b* located between the outer cuts 202 and intermediate cuts 204*a* and 204*b*, and inner sections 214*a*, 214*b* between the outer cuts 202 and intermediate cuts 208. Although additional and different cuts from the cuts 202, 204, 208, and 210 may be made on the pad 103, these cuts represent examples of types and locations of cuts that can be used to size a pad in a dimensionally-independent manner. Types of cuts that can be made on the pad 103 include, for example, arcuate, circular, ovoid, zigzag, and/or linear cuts. Further, although the cuts shown here are along the length L and width W of the pad, similar cuts may be made along the thickness T of pad 103, such that a thinner pad can be used in a wound site. Cuts may also be made at an angle not aligned with either of the X, Y, or Z axes, for example diagonally across the pad 103.

In use, the pad 103 may be too large for the wound site 110, and may need to be sized by removing the detachable area 218 encompassed by the edges of the pad 103 and the cuts 202 made thereon. For smaller wounds, detachable areas 212*a*, 212*b*, 214*a*, and 214*b* may all be removed to leave only the detachable areas 216 and 217. In even smaller wounds, the remainder of the pad 103 may be removed to leave only the central detachable area 216. Typically, such sizing can be performed manually, for example using scissors, but such methods incur concomitant disadvantages such as difficulties in manipulating a cutting utensil in a busy operating room, uneven and imprecise cuts, and the possibility of shedding foreign particles into a wound site. Instead, the premade cuts on the pad 103 may be detached by hand or with minimal cutting along the various bridge portions 206, 220, 222.

With continued reference to FIGS. 3-5, certain embodiments permit sizing of a pad 103 in a dimensionally-independent manner. Here, sections from the pad 103 can be detached or cut along the delineations between the various cuts, for example the sections 212*a*, 212*b* and 214*a*, 214*b*. These cuts 204 and 208 permit sizing of the pad 103 as desired to more closely tailor the actual dimensions of a wound site. For example, sizing a pad 103 for fitting in a wound that is wider on the left side and narrower on the right side may be effectuated by removing a pad section 214*a* delineated between the cuts 208*a*, 208*b* and 202*a*, 202*b*. In another example, where the pad 103 is longer along its top portion than the wound site 110, a pad section 212*a*, delineated between cuts 202*a*, 202*b*, and 204*a* can be removed from one end of the pad 103. In these preceding examples, the outer detachable portion 218 has preferably already been removed, although this is not necessarily required. Consequently, dimensionally-independent sizing of the pad 103 (e.g., modifying the length of the pad without altering the width of the pad, and vice-versa) may be achieved by detaching sections 212, 214 delineated by cuts 204 or 208. Additional detachable sections encompassed by additional cuts so as to permit dimensionally-independent sizing of the pad 103 are contemplated, and the embodiments illustrated herein are not intended to be limiting. Obviously, for smaller wound sites, the removal of symmetric sections of the pad 103 may still be useful, and embodiments of the pad 103 may provide such sections, illustrated here as sections 218, 217, 216. For example, removal of the outer section 218 of the pad 103 along the cuts 202 may be necessary. Similarly, for smaller incisions only the inner section 216 delineated inside cuts 210 may be required.

FIGS. 6-56 illustrate several different embodiments and views of an organ protection layer 105. As stated previously, such an organ protection layer 105 is preferably designed and constructed so as to be minimally adherent to a wound site, and more preferably non adherent to a wound site. In the case of an abdominal wound, the organ protection layer 105 is preferably minimally adherent or non-adherent to exposed viscera and other internal organs. The organ protection layer 105 is more preferably constructed from a flexible material, for example polymers such as polyurethane (including Elastollan®), polyethylene, polytetrafluoroethylene, or blends thereof.

The organ protection layer 105 is preferably larger than the foam pad 103, because when used, the organ protection layer 105 may then be tucked around and into a wound site. For example, when used in an abdominal wound, the organ protection layer 105 is preferably inserted into the abdominal cavity between the bowels. Preferably, the organ protection layer 105 is arranged so as to prevent the pad 103 from contacting abdominal viscera and other internal organs, although contact with the edges of the abdominal incision may be acceptable.

In the course of treatment using the system described above, the organ protection layer 105 is preferably permeable, for example provided with openings such as holes, slits, or channels. These openings may be useful in particular in the treatment of abdominal compartment syndrome, where these openings can be used to channel the often-copious amounts of exudate and other fluids that may be produced. In addition to aiding in the removal of exudate and other fluids from a wound site, the openings are useful for transmitting and distributing negative pressure to the wound site. Preferably, the openings are small enough to prevent the ingrowth of tissue, but large enough to prevent occlusion. Additionally, some embodiments of the organ protection layer 105 can be provided with a microperforated organ protection layer. Different embodiments of the organ protection layer 105 (for example as illustrated in FIGS. 6, 11, 16, 21, 26, 32, 37, 42, 47, 52) may also confer advantages during manufacturing, such as ease of production. Manufacturing of the organ protection layer 105 can entail cutting slits or holes for example with a die or die-cutting knives, rotary perforators, water jets, laser cutting, or ultrasonically.

Treatment of wounds with negative pressure generally requires that the wound be cleaned in a medically-acceptable manner, optionally filled with a wound packing material of some sort (such as foam), sealed with a drape, and connected to a source of negative pressure. The treatment of wounds exposing internal organs, blood vessels, and nerves, and in particular those in the abdominal cavity, may necessitate particular considerations. First, typical wound packing materials such as foam or gauze may desirably not be placed in direct contact with abdominal viscera such as the intestines or stomach, as these materials may undesirably adhere to the viscera. Instead, a non- or minimally-adherent organ protection layer 105, described previously, is preferably placed in the abdominal cavity or wound site 110. This organ protection layer 105 is preferably cut to size (if necessary), and tucked between the viscera and the abdominal fascia, with any excess material folded up over itself to avoid trapping any of the abdominal contents. Subsequently, the foam pad 103, after being sized as described above, is placed over the organ protection layer and preferably toward the middle of the wound site 110. A drape 107, again as described above, is cut to size (if necessary) and preferably placed such that it overlaps onto at least a portion of healthy skin surrounding the wound site 110. In some cases, if one drape 107 is insufficient, additional drapes may be provided; these are preferably overlapped at least partially so as to permit a secure seal to be made. Preferably, the drape 107 is provided with an adhesive layer on its underside, which may be protected by a backing layer. Such a backing layer is preferably removed before use so as to permit the drape 107 to be adhered to the skin surrounding the wound site as well as to the foam pad 103. An aperture 109 may then be made through the drape 107, although some embodiments may comprise a drape 107 supplied with one or more pre-made aperture or apertures 109. A conduit 112 connected to a source of negative pressure may then be connected to the aperture 109, or, in some embodiments, under a side of the drape 107, such that a fluidic connection between the wound site 110 and the source of negative pressure is created. The fluidic connection permits the therapeutic application of negative pressure to the wound site 110, and may be applied as necessary until the wound site 110 has reached a desired level of healing or until another surgical intervention is required.

The Drainage Layer(s) of FIGS. 57-63

Typically, in negative pressure wound therapy (NPWT) applied to the open abdomen, hydrophobic foams and/or hydrophobic organ protection layers are used as the underlying layers. Commercially available organ protection layers are sold by both Smith & Nephew, Inc. under the RENASYS® brand and by Kinetic Concepts Inc. However, as will be understood by one of skill in the art, the organ protection layer (typically a film) may be constructed of any materials disclosed herein this section or elsewhere in the specification, for example: polytetrafluoroethylene, polyurethane (including Elastollan®), polyethylene, polytetrafluoroethylene, or blends thereof. Hydrophobic materials are capable of providing fluid path for liquid from the abdomen with good distribution of negative pressure.

However, hydrophobic materials' ability to permit flow of aqueous liquid may be limited by their inherent absence of affinity with fluid. Instead, hydrophilic materials may provide an advantage in drawing liquid out of wound site over hydrophobic materials due to their ability to absorb and direct flow of aqueous fluid via capillary action (also known as "wicking fluid") to the overlying suction conduit such as described elsewhere in the specification. In the case of porous structures such as foams, effective flow of aqueous fluid through compressed small pores are required to effectively remove wound fluid in negative pressure wound therapy (NPWT), and capillary force drives spontaneous flow of liquid through pores. Such phenomenon is referred to as wicking. Hydrophilic materials have superior wetting ability and capillary action over hydrophobic materials. Therefore, porous structures made of hydrophilic materials in some embodiments can be more effective at wicking liquid through the system of small interconnected pores under a negative pressure than similar structures made of hydrophobic materials. In addition to hydrophilic materials, materials comprising an acquisition distribution material, DryWeb TDL2, SlimCore TL4, or the like may have similar property of wicking fluid and may have ability to transport liquid while transmitting negative pressure. Due to the capillary action, such materials may even draw fluid from a tissue site without the need for negative pressure.

Further, hydrophilic materials may be placed directly on underlying organs without the formation of undesirable granulation tissue. The ability to directly contact the tissue brings multiple advantages. For example, the foam can be cut directly according to the shape and size of the wound tissue. Further, the direct contact between the foam and the tissue provides intimate liquid to liquid path contact.

Figure 57:
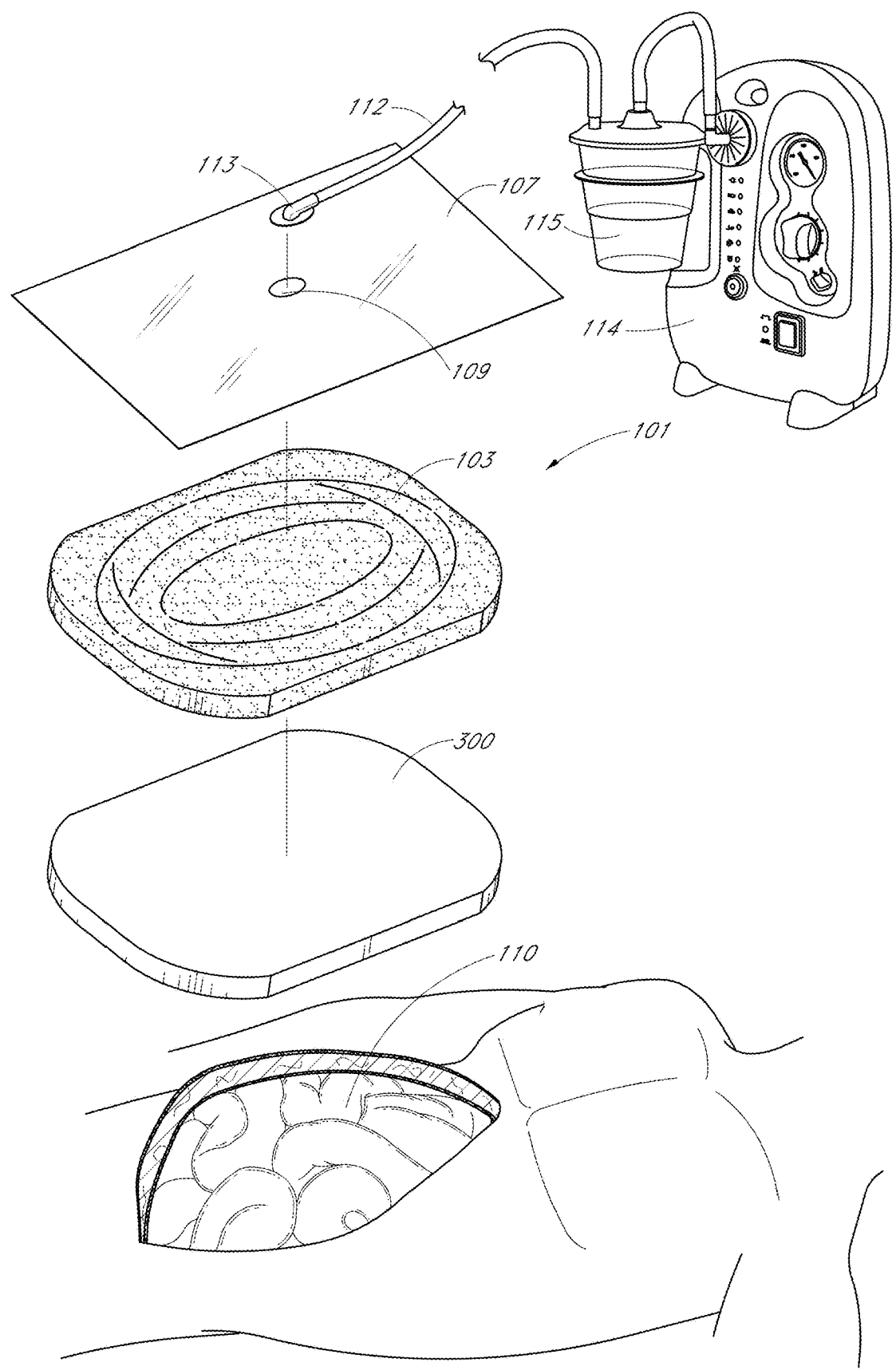
FIG. 57 is a schematic illustration of an embodiment a system for the treatment of abdominal wounds.

In certain embodiments, and as shown in FIG. 57, a drainage layer 300 may be placed directly against the underlying organs as the bottom-most layer in a typical NPWT set-up, using many of the components described in FIG. 1. In some embodiments, the drainage layer may be a hydrophilic foam, such as a polyvinyl alcohol (PVA) foam. Such foams are also commonly known as WhiteFoam in contrast to typical hydrophobic foams called "black foams." In some embodiments, such as depicted in FIG. 57, the drainage layer may replace the organ protection layer, similar to the organ protection layers depicted in FIGS. 6-56 and elsewhere in the specification. Alternatively, the drainage layer 300 may be placed above and/or below the separate organ protection layer similar to the organ protection layers depicted in FIGS. 6-56 and elsewhere in the specification. In embodiments where drainage layers are both above and below the organ protection layer, one or more drainage layers may be used. In some embodiments, the drainage layer may comprise a film layer applied to a foam (hydrophilic or hydrophobic) layer. Such films may be identical to the organ protection layers 105 described herein this section or elsewhere in the specification, such as in FIGS. 6-56. For example, film layers may be constructed so as to be minimally adherent or non-adherent to a wound site and may be constructed from a flexible material, such as polyurethane (including Elastollan®), polyethylene, polytetrafluoroethylene, or blends thereof. Film layers may have openings such as holes, slits, or channels as described in relation with FIGS. 6-56. In certain embodiments, the films may comprise patterns and shapes not shown in FIGS. 6-56.

The drainage layer 300 may be made of various suitable materials with varying properties, such as described herein this section or elsewhere in the specification. For example, in some embodiments, the drainage layer may be made to have a high tensile strength combined with lower frangibility. Lower frangibility may be desirable to reduce the shedding of cut particulates into the abdomen when the drainage layer is shaped by a medical practitioner. Additionally, high mechanical strength allows for the use of very thin drainage layers which makes placement of the drainage layer easier. One of skill in the art will further understand that the drainage layers described herein this section and elsewhere in the specification may be shaped in any suitable manner. For example, the drainage layers may be shaped to better fit the shape and size of the wound, such as an oval and/or oculiform shape.

The foam layers and/or drainage layers described in this section may have the shape and frangibility of any foam layers and/or drainage layers described herein this section or elsewhere in the specification, such as in FIGS. 2-5. For example, in some embodiments, the drainage layer is provided with a thickness less than its width and length. As will be further understood by one of skill in the art, any configuration of the organ protection layer and/or film layer against a foam layer may be applied to one or both sides of the foam layer and/or the edges. In some embodiments, the film layer may be applied on the bottom of the foam layer so that the foam can directly contact with fascia. In other embodiments, the film layer may be applied to only the top of the foam, or on both the top and the bottom and/or the edges. In some embodiments, the film layer may be pre-attached to the foam layer. In further embodiments, the film layers are configured to be easily dispensed by practitioners depending on clinical outcomes. In some embodiments, the drainage layer may comprise one or more perforations described herein this section or elsewhere in the specification, such as in FIGS. 2-3. In some embodiments, wherein the drainage layer comprises the film layer, such perforations may extend across the thickness of the film layer.

Figure 58:
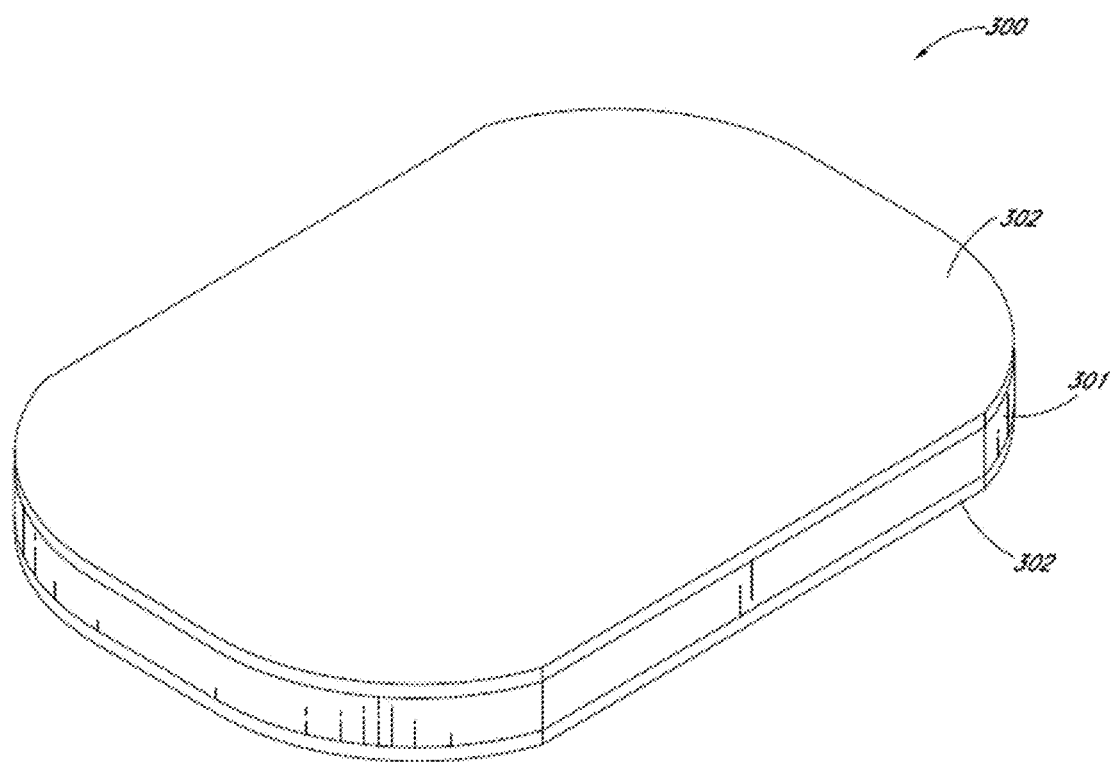
FIGS. 58-60 illustrate an embodiment of a drainage layer.
Figure 59:
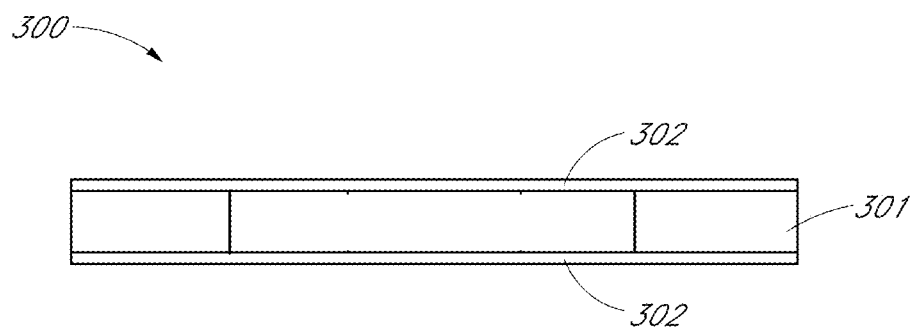
Figure 60:
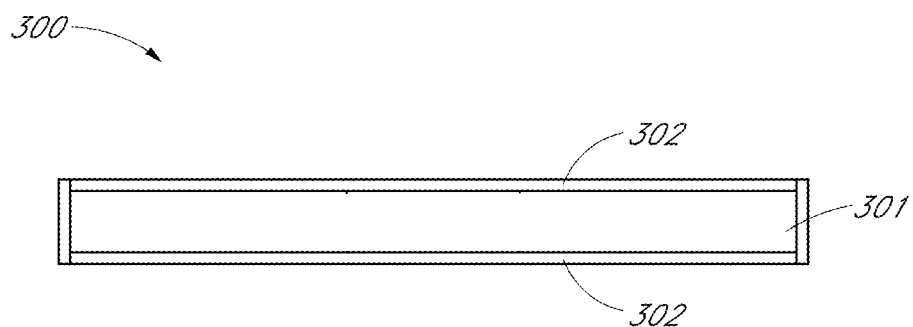

In some embodiments, as shown by FIGS. 58-60, the drainage layer may comprise a foam layer sandwiched between film layers. FIG. 58 depict a perspective view of an embodiment where a thin layer of PVA foam 301 is sandwiched between two film layers 302. FIG. 59 depicts a side view of this embodiment. In some embodiments, the top and bottom film layers 302 may be sealed to each other and inner hydrophilic foam 301 layer may be completely encased by film layers 302 as shown by FIG. 60 illustrating a cross-sectional view of such embodiments. In embodiments, the film layers 302 may be partially welded together at the edges. In some embodiments, the film layers 302 may be spot-welded together, thereby creating fluid channels. The welds may be only at the edges of the films or may extend into the films, thereby creating channels that extend inward, such as depicted below in relation to FIG. 61. Such channels may also be coupled with a central opening, thereby channeling fluid from the edges of the welded film sandwich into the center where it can be drawn into the conduit and beyond via negative pressure.

Figure 61:
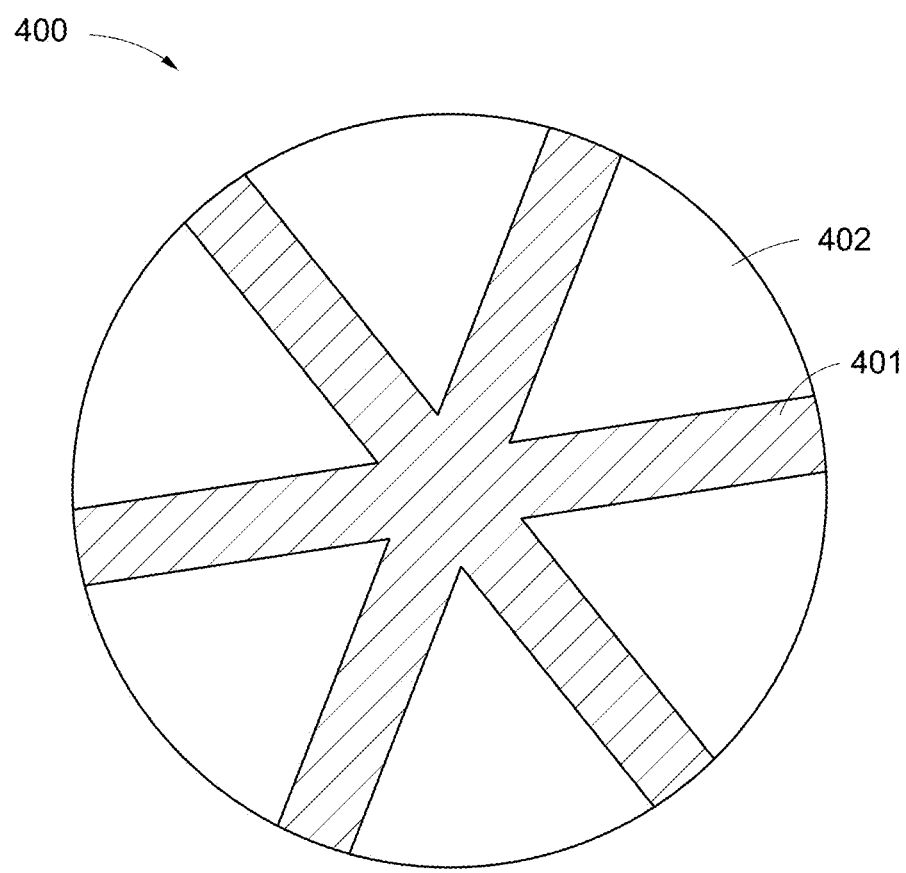
FIGS. 61-62 illustrate embodiments of a drainage layer.

In some embodiments of the drainage layer, a film layer above or below a foam layer may not fully cover the entirety of the foam surface. For example, the film layer may cover less than 100%, 90%, 70%, 50%, 30% or 10% of the surface area of the bottom surface and/or the top surface of the hydrophilic foam. FIG. 61 depicts a top view of an embodiment of a drainage layer 400, similar to the drainage layer depicted above in FIGS. 58-60. The film layer 402 in FIG. 61 covers portions of the foam layer, leaving exposed foam 401 forming channels roughly in the shape of an asterisk. Even though the drainage layer of the embodiment shown by FIG. 61 is circle-shaped, in some embodiments, the drainage layer 400 may be elliptical-shaped, or may have any other suitable shapes. Even though the embodiment of FIG. 61 has three channels, some embodiments may have four, five, six, seven, eight or more channels. In certain embodiments, the channels may crisscross the surface of the drainage layer in different patterns such as a spiral, cross-hatch, or starfish.

Figure 62:
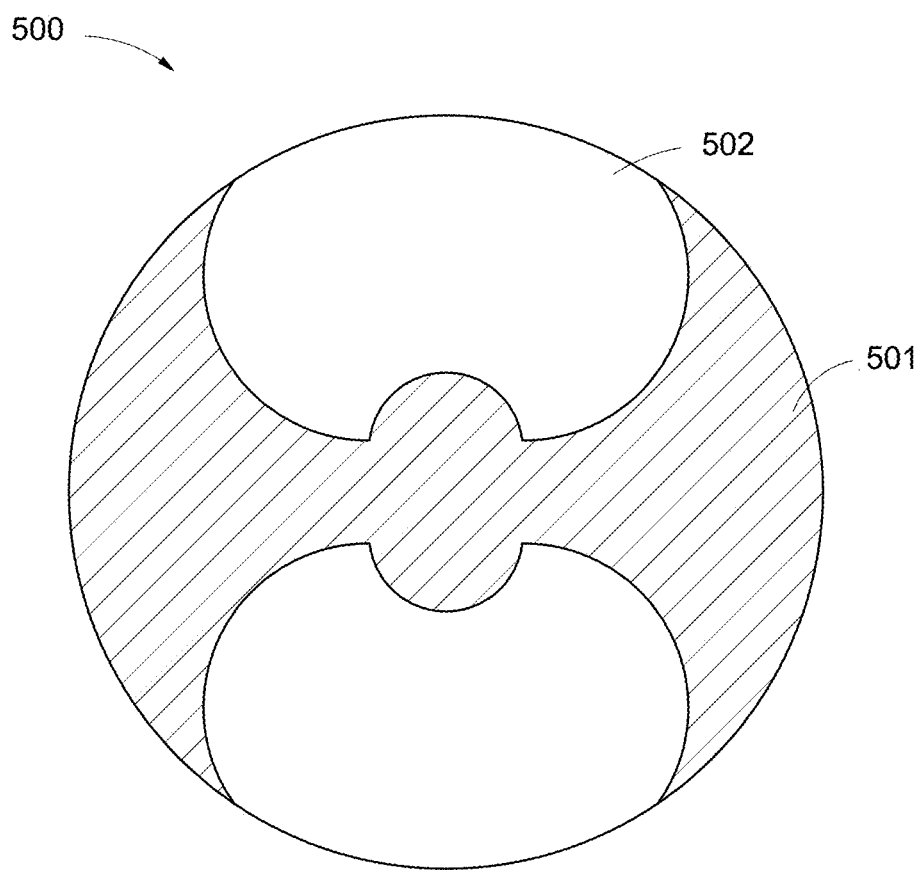

However, the patterns are not limited to such shapes, and the film may uncover the foam layer in any suitable shape for desired use. For example, FIG. 62 depicts a "lobed" embodiment of the drainage layer 500 where lobes of the foam layer 501 are uncovered by the film 502. When the drainage layer is placed over the abdominal organs, the lobe-shaped uncovered portion 501 allows the foam to easily reach into abdominal cavity, such as the paracolic gutters, and directly contact and absorb peritoneal fluid built up there, while the portion covered by the film 502 helps prevent formation of granulation tissue and channel fluid from the lobes into the center where it can be drawn into the conduit and beyond via negative pressure. Even though the embodiment of FIG. 62 is circle-shaped, the drainage layer may have various shapes to better accommodate to the wound site. For example, in some embodiments, the drainage layer 500 may be elliptical-shaped in left-right, such that the uncovered portion 501 is on opposite ends of the major axis. In other embodiments, the drainage layer 500 may be elliptical-shaped in up-down, such that the covered portion 502 is on opposite ends of the major axis.

Even though film layers 402 or 502 in FIGS. 61-62 do not show any patterns, for the embodiments of the drainage layer where the hydrophilic foam layer is partially covered by film layers, the film layers may have openings such as holes, slits, or channels as described in relation with FIGS. 6-56 or elsewhere in the specification. In some embodiments, film layers on the top and the bottom of the hydrophilic foam partially covering respective surfaces of the hydrophilic foam are in same pattern. The film layers may be sealed or wrapped around at side walls of the hydrophilic foam. In other embodiments, only one of the top or the bottom surface of the hydrophilic foam may be partially covered by the film layer, while the other surface of the hydrophilic foam may be fully covered or fully uncovered. The side wall of the hydrophilic foam may be fully completely covered, completely uncovered or partially covered.

Figure 63:
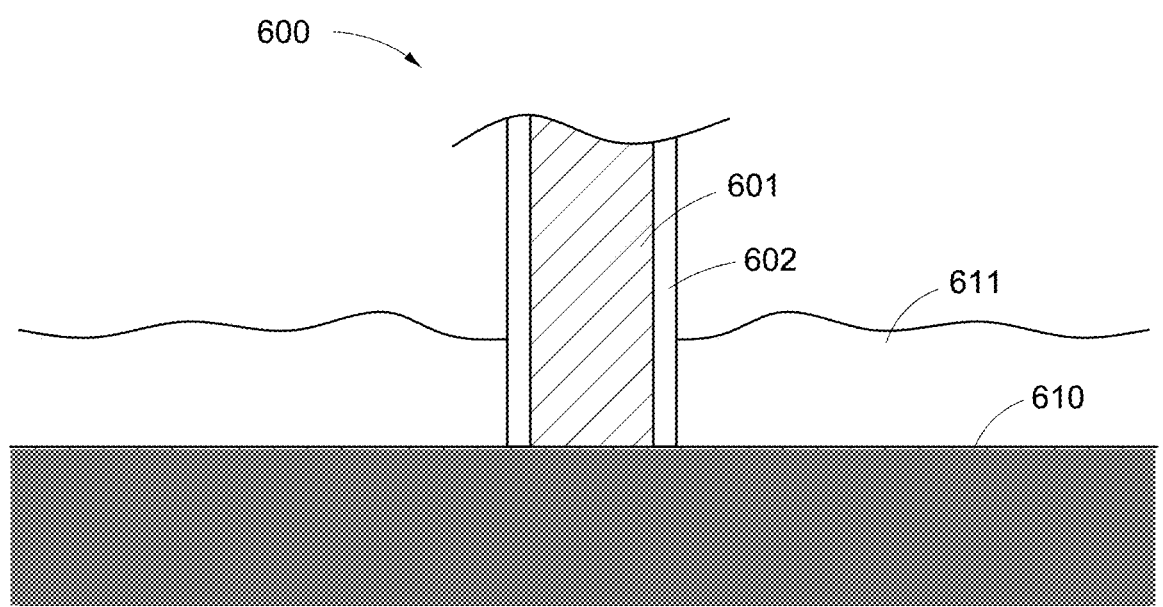
FIG. 63 illustrates an embodiment of a drainage layer.

In some embodiments, as shown by FIG. 63, the drainage layer 600 can be oriented 90 degrees from the embodiments of FIGS. 58-62 when placed in a wound. In FIG. 63, the side wall of the foam layer 601 directly contacts the underlying tissue 610, thereby allowing the foam layer to act as a vertical channel to draw fluid 611 away from the tissue site. In some embodiments, the foam layer 601 may also be surrounded on either side by film layers 602. Film layer 602 may fully or partially cover faces of the foam layer 601 in any fashion described in this section or elsewhere. In some embodiments, film layer 602 fully covers the foam layer 601, so that only side wall of the foam layer is exposed and the foam layer only directly contact with the underlying tissue 610. In some embodiments, film layer(s) may partially expose faces of foam layer 601, so that wound fluid 611 that was built up above wound tissue can directly contact the foam layer 601 and be absorbed by the foam.

It should be understood by those skilled in the art that hydrophilic material or hydrophilic foam in embodiments described in this section or elsewhere in this application can be substituted for, or combined with other materials or structures having similar fluid-drawing ability, such as an acquisition distribution material, DryWeb TDL2, SlimCore TL4, or the like. Further, an acquisition distribution material may be composed of multiple fiber types and be complex in structure and design. The acquisition distribution material may comprise a plurality of loosely packed fibers, which may be arranged in a substantially horizontal or vertical fibrous network. In some embodiments, the acquisition distribution material may consist of a mix of two fiber types. The acquisition distribution material may contain a cellulosic based material, a polyethylene (PE) type material, polyethylene terephthalate (PET), or mixture thereof. The PE/PET fibers may have a smooth surface morphology, while the cellulosic fibers may have a relatively rougher surface morphology. In some embodiments the acquisition distribution material may comprise about 60% to about 90% cellulosic fibers, for example approximately 75% cellulosic fibers, and may comprise about 10% to about 40% PE/PET fibers, for example approximately 25% PE/PET fibers.

Further, the drainage layer described in this section or elsewhere in this application may comprise multiple internal layers. For example, in certain embodiments, an internal layer of the drainage layer may be constructed to advantageously vertically wick fluid, while the other internal layer may be constructed to advantageously horizontally wick fluid. In some materials, multiple internal layers may be constructed from different materials.

The foregoing description is that of certain features, aspects and advantages of the present invention, to which various changes and modifications can be made without departing from the spirit and scope of the present invention. Moreover, the negative pressure treatment system disclosed herein need not feature all of the objects, advantages, features and aspects discussed above. Those of skill in the art will recognize that the invention can be embodied or carried out in a manner that achieves or optimizes one advantage or a group of advantages as taught herein without necessarily achieving other objects or advantages as may be taught or suggested herein. For example, in some embodiments the pad 103 can be used without the organ protection layer 105 and/or drape 107. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed negative pressure treatment system.

Although this disclosure describes certain embodiments, it will be understood by those skilled in the art that many aspects of the methods and devices shown and described in the present disclosure may be differently combined and/or modified to form still further embodiments or acceptable examples. All such modifications and variations are intended to be included herein within the scope of this disclosure. Indeed, a wide variety of designs and approaches are possible and are within the scope of this disclosure. No feature, structure, or step disclosed herein is essential or indispensable. Moreover, while illustrative embodiments have been described herein, the scope of any and all embodiments having equivalent elements, modifications, omissions, combinations (e.g., of aspects across various embodiments), substitutions, adaptations and/or alterations as would be appreciated by those in the art based on the present disclosure. While certain embodiments have been described, these embodiments have been presented by way of example only, and are not intended to limit the scope of protection.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A system for the treatment of a wound site using negative pressure, the system comprising:
    a porous pad suitable for the transmission of negative pressure to the wound site;
    a drainage layer positioned under the porous pad, the drainage layer configured to channel fluid from the wound site;
    a flexible drape configured to be placed over the porous pad;
    a source of negative pressure;
    a conduit configured to transmit negative pressure from the source to the flexible drape; and
    wherein the drainage layer comprises a hydrophilic foam and one or more film layers, the one or more film layers comprising a channel extending from an edge of the drainage layer to a center of the drainage layer such that the hydrophilic foam beneath the channel is uncovered by the one or more film layers.

2. The system of claim 1, wherein the hydrophilic foam comprises polyvinyl alcohol (PVA).

3. The system of claim 1, wherein the drainage layer comprises a top film layer over the hydrophilic foam.

4. The system of claim 1, wherein the drainage layer comprises a bottom film layer under the hydrophilic foam.

5. The system of claim 1, wherein the one or more film layers comprise a material selected from the group comprising polyurethane, polyethylene, polytetrafluoroethylene, or blends thereof.

6. The system of claim 1, wherein the one or more film layers cover at least part of a side wall of the drainage layer.

7. The system of claim 1, wherein the one or more film layers covers less than 100% of a surface area of a bottom surface and/or a top surface of the hydrophilic foam.

8. The system of claim 7, wherein the one or more film layers cover less than 70% of the surface area of the bottom surface and/or the top surface of the hydrophilic foam.

9. The system of claim 8, wherein the one or more film layers cover less than 30% of the surface area of the bottom surface and/or the top surface of the hydrophilic foam.

10. The system of claim 7, wherein an uncovered portion of the hydrophilic foam layer is in the shape selected from the group consisting of asterisk shape, spiral shape, crosshatch shape, starfish shape, and lobe shape.

11. The system of claim 1, wherein the drainage layer is provided with a thickness less than its width and length, wherein the drainage layer further comprises at least one cut extending through at least a portion of the thickness of the drainage layer to define a section detachable from the drainage layer to permit the drainage layer to be sized in a dimensionally-independent manner wherein the length and the width of the drainage layer can be modified independently of each other.

12. The system of claim 1, further comprising an organ protection layer.

13. The system of claim 1, further comprising a port attachable to an aperture formed in the drape and the conduit.

14. A method of treating a wound site using negative pressure, wherein the treatment comprises:
    placing a hydrophilic drainage layer onto the wound site, the drainage layer comprising a hydrophilic foam and a film layer, the film layer comprising a channel extending from an edge of the drainage layer to a center of the drainage layer such that the hydrophilic foam beneath the channel is uncovered by the film layer;
    placing a porous pad over the hydrophilic drainage layer;
    sealing the wound site with a flexible drape positioned over the wound and sealed to the skin surrounding the wound; and
    applying negative pressure to the wound site from a source of negative pressure, wherein the source of negative pressure is applied through a conduit fluidically connected between the drape and the source of negative pressure.

15. The method of claim 14, wherein the hydrophilic drainage layer comprises a polyvinyl alcohol (PVA) foam.

16. The method of claim 14, wherein the treatment further comprises placing an organ protection layer onto the wound site.

17. The method of claim 14, wherein the hydrophilic drainage layer comprises an organ protection layer.

18. The method of claim 14, wherein the side wall of the hydrophilic drainage layer touches onto the wound site.

19. The system of claim 1, further comprising an acquisition distribution layer positioned adjacent the drainage layer, the acquisition distribution layer comprising a plurality of fibers and configured to wick fluid.

\* \* \* \* \*